US011291382B2

(12) United States Patent
Vaezi et al.

(10) Patent No.: US 11,291,382 B2
(45) Date of Patent: Apr. 5, 2022

(54) SYSTEM AND METHOD FOR DETECTING AND MEASURING THE CONDITION OF INTRALUMINAL ESOPHAGEAL MUCOSA

(71) Applicants: Diversatek Healthcare, Inc., Milwaukee, WI (US); Vanderbilt University, Nashville, TN (US)

(72) Inventors: Michael F. Vaezi, Brentwood, TN (US); Charles Lindsay, Monument, CO (US); James M. Prinster, Littleton, CO (US)

(73) Assignees: Diversatek Healthcare, Inc., Milwaukee, WI (US); Vanderbilt University, Nashville, TN (US)

( * ) Notice: Subject to any disclaimer, the term of this patent is extended or adjusted under 35 U.S.C. 154(b) by 252 days.

(21) Appl. No.: 16/429,992

(22) Filed: Jun. 3, 2019

(65) Prior Publication Data
US 2019/0365276 A1 Dec. 5, 2019

Related U.S. Application Data

(60) Provisional application No. 62/725,070, filed on Aug. 30, 2018, provisional application No. 62/679,604, filed on Jun. 1, 2018.

(51) Int. Cl.
*A61B 5/0538* (2021.01)
*A61B 5/03* (2006.01)
(Continued)

(52) U.S. Cl.
CPC ............ *A61B 5/0538* (2013.01); *A61B 5/037* (2013.01); *A61B 5/14539* (2013.01);
(Continued)

(58) Field of Classification Search
CPC ....... A61B 5/0538; A61B 5/053; A61B 5/037; A61B 5/1076; A61B 5/4211;
(Continued)

(56) References Cited

U.S. PATENT DOCUMENTS

| 4,587,975 A | 5/1986 | Salo et al. |
| 4,706,688 A | 11/1987 | Don Michael et al. |

(Continued)

FOREIGN PATENT DOCUMENTS

WO 2009113064 A2 9/2009

OTHER PUBLICATIONS

Agoritsas, et al., Does Prevalence Matter to Physicians in Estimating Post-test Probability of Disease? A Randomized Trial, J Gen Intern Med, 2011, 26:373-378.
(Continued)

*Primary Examiner* — Devin B Henson
(74) *Attorney, Agent, or Firm* — Quarles & Brady LLP

(57) ABSTRACT

Disclosed are catheter systems and methods of using the catheter system to acquire mucosal impedance data of a patient. Also disclosed are methods of classifying or otherwise identifying esophageal conditions in a subject based on mucosal impedance data acquired using a catheter system. Unlike conventions systems that require subjective input from a physician to render a diagnosis, the systems and methods described herein can utilize the mucosal impedance measurements to generate a probability that the subject's esophagus corresponds to an esophageal condition or a set of esophageal conditions. In one embodiment, a classification model is used to generate the probability. The classification model may generate the probability based at least in part on a change in the mucosal impedance measurements between a distal location and a proximal location on the subject's esophagus.

12 Claims, 9 Drawing Sheets

(51) Int. Cl.
  *A61B 5/00* (2006.01)
  *A61B 5/145* (2006.01)
  *A61M 25/10* (2013.01)

(52) U.S. Cl.
  CPC .......... *A61B 5/4211* (2013.01); *A61B 5/4233* (2013.01); *A61B 5/6853* (2013.01); *A61B 5/7264* (2013.01); *A61M 25/1018* (2013.01)

(58) Field of Classification Search
  CPC ..... A61B 5/4233; A61B 5/6853; A61B 5/687; A61B 5/6885; A61B 5/7264; A61B 5/7203; A61B 5/7221; A61B 5/7246; A61B 5/7275; A61M 25/1018
  See application file for complete search history.

(56) References Cited

U.S. PATENT DOCUMENTS

| | | | |
|---|---|---|---|
| 4,809,710 | A | 3/1989 | Williamson |
| 4,840,182 | A | 6/1989 | Carlson |
| 4,852,580 | A | 8/1989 | Wood |
| 4,981,470 | A | 1/1991 | Bombeck, IV |
| 5,024,228 | A | 6/1991 | Goldstone et al. |
| 5,056,532 | A | 10/1991 | Hull et al. |
| 5,087,244 | A | 2/1992 | Wolinsky et al. |
| 5,109,870 | A | 5/1992 | Silny et al. |
| 5,479,935 | A | 1/1996 | Essen-Moller |
| 5,551,439 | A | 9/1996 | Hickey |
| 5,553,611 | A | 9/1996 | Budd et al. |
| 5,617,876 | A | 4/1997 | van Duyl |
| 5,687,737 | A | 11/1997 | Branham et al. |
| 5,769,846 | A | 6/1998 | Edwards et al. |
| 5,782,774 | A | 7/1998 | Shmulewitz |
| 5,791,349 | A | 8/1998 | Shmulewitz |
| 5,833,625 | A | 11/1998 | Essen-Moller |
| 5,860,974 | A | 1/1999 | Abele |
| 6,006,755 | A | 12/1999 | Edwards |
| 6,095,987 | A | 8/2000 | Shmulewitz et al. |
| 6,104,941 | A | 8/2000 | Huey et al. |
| 6,292,689 | B1 | 9/2001 | Wallace et al. |
| 6,315,733 | B1 | 11/2001 | Zimmon |
| 6,358,245 | B1 | 3/2002 | Edwards et al. |
| 6,666,828 | B2 | 12/2003 | Greco et al. |
| 6,728,562 | B1 | 4/2004 | Budd et al. |
| 6,882,879 | B2 | 4/2005 | Rock |
| 6,965,795 | B2 | 11/2005 | Rock |
| 6,974,456 | B2 | 12/2005 | Edwards et al. |
| 7,184,812 | B2 | 2/2007 | Sinderby et al. |
| 7,236,820 | B2 | 6/2007 | Mabary et al. |
| 7,454,244 | B2 | 11/2008 | Kassab et al. |
| 7,476,204 | B2 | 1/2009 | Parks et al. |
| 7,555,329 | B2 | 6/2009 | Gross et al. |
| 7,585,296 | B2 | 9/2009 | Edwards et al. |
| 7,654,997 | B2 | 2/2010 | Makower et al. |
| 7,736,320 | B2 | 6/2010 | Tsukashima et al. |
| 7,818,155 | B2 | 10/2010 | Stuebe et al. |
| 7,856,277 | B1 | 12/2010 | Thacker et al. |
| 8,103,338 | B2 | 1/2012 | Harlev et al. |
| 8,106,905 | B2 | 1/2012 | Markowitz et al. |
| 8,224,422 | B2 | 7/2012 | Mottola et al. |
| 8,306,290 | B2 | 11/2012 | Parks |
| 8,371,303 | B2 | 2/2013 | Schaner et al. |
| 8,386,010 | B2 | 2/2013 | Beetel et al. |
| 8,521,249 | B2 | 8/2013 | O'Dea |
| 8,551,096 | B2 | 10/2013 | Perry et al. |
| 8,568,336 | B2 | 10/2013 | Gewolb et al. |
| 9,814,408 | B2 | 11/2017 | Mabary et al. |
| 2004/0171942 | A1 | 9/2004 | Ackerman et al. |
| 2004/0215296 | A1 | 10/2004 | Ganz et al. |
| 2004/0230110 | A1 | 11/2004 | Sinderby et al. |
| 2004/0254495 | A1 | 12/2004 | Mabary et al. |
| 2005/0065450 | A1 | 3/2005 | Stuebe et al. |
| 2005/0080832 | A1 | 4/2005 | Stuebe et al. |
| 2006/0004304 | A1 | 1/2006 | Parks |
| 2006/0015162 | A1 | 1/2006 | Edward et al. |
| 2006/0095032 | A1 | 5/2006 | Jackson et al. |
| 2006/0116564 | A1 | 6/2006 | Mintchev et al. |
| 2006/0178587 | A1 | 8/2006 | Khoury |
| 2006/0282071 | A1 | 12/2006 | Utley et al. |
| 2007/0135809 | A1 | 6/2007 | Utley et al. |
| 2007/0225613 | A1 | 9/2007 | Mabary et al. |
| 2008/0004547 | A1 | 1/2008 | Dinsmoor et al. |
| 2008/0033316 | A1 | 2/2008 | Kassab et al. |
| 2008/0077043 | A1 | 3/2008 | Malbrain et al. |
| 2008/0121231 | A1 | 5/2008 | Sinderby et al. |
| 2008/0125772 | A1 | 5/2008 | Stone et al. |
| 2008/0161730 | A1 | 7/2008 | McMahon et al. |
| 2008/0188912 | A1 | 8/2008 | Stone et al. |
| 2008/0194996 | A1 | 8/2008 | Kassab |
| 2008/0306411 | A1 | 12/2008 | Stuebe et al. |
| 2008/0319350 | A1 | 12/2008 | Wallace et al. |
| 2009/0012512 | A1 | 1/2009 | Utley et al. |
| 2009/0062684 | A1 | 3/2009 | Gregersen et al. |
| 2009/0118637 | A1 | 5/2009 | Kassab et al. |
| 2009/0124937 | A1 | 5/2009 | Parks |
| 2009/0131928 | A1 | 5/2009 | Edwards et al. |
| 2009/0192405 | A1 | 7/2009 | Carney |
| 2009/0240162 | A1 | 9/2009 | Stuebe et al. |
| 2009/0306589 | A1 | 12/2009 | Tilson et al. |
| 2010/0004648 | A1 | 1/2010 | Edwards et al. |
| 2010/0113939 | A1 | 5/2010 | Mashimo et al. |
| 2010/0125239 | A1 | 5/2010 | Perry et al. |
| 2010/0137738 | A1 | 6/2010 | Beetel et al. |
| 2010/0160906 | A1 | 6/2010 | Jarrard |
| 2010/0168743 | A1 | 7/2010 | Stone et al. |
| 2010/0191089 | A1 | 7/2010 | Stebler et al. |
| 2010/0204560 | A1 | 8/2010 | Salahieh et al. |
| 2010/0234840 | A1 | 9/2010 | Jackson et al. |
| 2010/0268110 | A1 | 10/2010 | Beltran et al. |
| 2010/0305479 | A1 | 12/2010 | O'Dea |
| 2011/0306897 | A1 | 12/2011 | Imran |
| 2012/0016256 | A1* | 1/2012 | Mabary .................. A61B 5/037 600/547 |
| 2012/0209086 | A1 | 8/2012 | Beute |

OTHER PUBLICATIONS

Ates, et al., Mucosal Impedance Discriminates GERD From Non-GERD Conditions, Gastroenterology, 2015, 148:334-343.

Caviglia, et al., Dilated Intercellular Spaces of Esophageal Epithelium in Nonerosive Reflux Disease Patients with Physiological Esophageal Acid Exposure, American Journal of Gastroenterology, 2005, 100(3):543-548.

Choksi, et al., Esophageal Mucosal Impedance Patterns Discriminate Patients With Eosinophilic Esophagitis From Patients With GERD, Clinical Gastroenterology and Hepatology, 2018, 16(5):664-671.

De Bortoli, et al., Association Between Baseline Impedance Values and Response Proton Pump Inhibitors in Patients With Heartburn, Clinical Gastroenterology and Hepatology, 2015, 13(6):1082-1088.

Dellon, et al., Variability in Diagnostic Criteria for Eosinophilic Esophagitis: A Systematic Review, American Journal of Gastroenterology, 2007, 102(10):2300-2313.

Dellon, et al., Clinical, Endoscopic, and Histologic Findings Distinguish Eosinophilic Esophagitis From Gastroesophageal Reflux Disease, Clinical Gastroenterology and Hepatology, 2009, 7:1305-1313.

Dellon, et al., ACG Clinical Guideline: Evidenced Based Approach to the Diagnosis and Management of Esophageal Eosinophilia and Eosinophilic Esophagitis (EoE), American Journal of Gastroenterology, 2013, 108:679-692.

Dellon, et al., Prevalence of Eosinophilic Esophagitis in the United States, Clinical Gastroenterology and Hepatology, 2014, 12:589-596.

Dent, et al., Epidemiology of Gastro-Oesophageal Reflux Disease: A Systematic Review, Gut, 2005, 54:710-71.

El-Serag, et al., Update on the Epidemiology of Gastro-Oesophageal Reflux Disease: A Systematic Review, Gut, 2014, 63(6):871-880.

(56) References Cited

OTHER PUBLICATIONS

Everhart, et al., Burden of Digestive Diseases in the United States Part I: Overall and Upper Gastrointestinal Diseases, Gastroenterology, 2009, 136:376-386.
Farre, et al., Evaluation of Oesophageal Mucosa Integrity by the Intraluminal Impedance Technique, Gut, 2011, 60(7):885-892.
Fass, et al., Effect of Ambulatory 24-Hour Esophageal pH Monitoring on Reflux-Provoking Activities, Digestive Diseases and Sciences, 1999, 44(11):2263-2269.
Fass, et al., Refractory GERD: What Is It?, Current Gastroenterology Reports, 2008, 10(3):252-257.
Fenter, et al., The Cost of Treating the 10 Most Prevalent Diseases in Men 50 Years of Age or Older, Am. J. Manag. Care, 2006, 12:S90-S98.
Furuta, et al., Eosinophilic Esophagitis, New England Journal of Medicine, 2015, 373:1640-1648.
Gonsalves, et al., Histopathologic Variability and Endoscopic Correlates in Adults with Eosinophilic Esophagitis, Gastrointestinal Endoscopy, 2006, 64(3):313-319.
Jensen, et al., Health-Care Utilization, Costs, and the Burden of Disease Related to Eosinophilic Esophagitis in the United States, American Journal of Gastroenterology, 2015, 110:626-632.
Katzka, et al., Effects of Topical Steroids on Tight Junction Proteins and Spongiosis in Esophageal Epithelia of Patients With Eosinophilic Esophagitis, Clinical Gastroenterogloy and Hepatology, 2014, 12(11):1824-1829.
Katzka, et al., Endoscopic Mucosal Impedance Measurements Correlate With Eosinophilia and Dilation of Intercellular Spaces in Patients With Eosinophilic Esophagitis, Clinical Gastroenterology and Hepatology, 2015, 13(7):1242-1248.
Kavitt, et al., The Role of Impedance Monitoring in Patients with Extraesophageal Symptoms, The Laryngoscope, 2013, 123(10):2463-2468.
Kessels, et al., Safety and Efficacy of Wireless pH Monitoring in Patients Suspected of Gastroesophageal Reflux Disease, Journal of Clinical Gastroenterology, 2017, 51(9):777-788.
Kessing, et al., Esophageal Acid Exposure Decreases Intraluminal Baseline Impedance Levels, American Journal of Gastroenterology, 2011, 106:2093-2097.
Kim, et al., Mo1132 Intraluminal Impedance Versus Mucosal Impedance Testing for the Diagnosis of GERD: Do They Measure the Same Thing?, Gastroeneterology, 2015, 148(4)(Suppl 1):S615-S616.
Lowry, et al., 704 An Innovative Mucosal Impedance Device Differentiates Active Eosinophilic Esophagitis From Inactive Disease, NERD and Controls, Gastrointestinal Endoscopy, 2016, 83(5), Supplement, p. AB166.
Lowry, et al., Mucosal Impedance Measurements Differentiate Pediatric Patients with Active vs Inactive Eosinophilic Esophagitis, J Pediatr Gastroenterol Nutr, 2018, 67(2):198-203.
Lundell, et al., Endoscopic Assessment of Oesophagitis: Clinical and Functional Correlates and Further Validation of the Los Angeles Classification, Gut, 1999, 45:172-180.
Lyman, et al., The Effect of Changing Disease Risk on Clinical Reasoning, Journal of General Internal Medicine, 1994, 9(9):488-495.
Odze, et al., Pathology of Eosinophilic Esophagitis: What the Clinician Needs to Know, American Journal of Gastroenterology, 2009, 104(2):485-490.
Pandolfino, et al., Ambulatory Esophageal pH Monitoring Using a Wireless System, American Journal of Gastroenterology, 2003, 98(4):740-749.
Pandolfino, et al., Comparison of the Bravo Wireless and Digitrapper Catheter-Based pH Monitoring Systems for Measuring Esophageal Acid Exposure, Am. J. Gastroenterol, 2005, 100(7):1466-1476.
Pandolfino, Esophageal Monitoring Devices, US Gastroenterology Review, 2007, pp. 23-26, Copyright Touch Briefings 2007, http://www.touchbriefings.com/pdf/2602/Pandolfino.pdf.
Patel, et al., Distal Mean Nocturnal Baseline Impedance on pH-Impedance Monitoring Predicts Reflux Burden and Symptomatic Outcome in Gastro-Oesophageal Reflux Disease, Alimentary Pharmacology and Therapeutics, 2016, 44:890-898.
Patel, et al., Novel Balloon Mucosal Impedance for Diagnosis of Gerd and EOE, Gastroenterology, 2017, 152:5, Supplement 1, p. S43.
Patel, et al., Utility of Esophageal Mucosal Impedance as a Diagnostic Test for Esophageal Disease, Current Opinion in Gastroenterology, 2017, 33(4):277-284.
Patel, et al., Su1084—Concordance Between Mucosal Impedance Measurements at Index Endoscopy and Wireless PH Monitoring: A Prospective Blinded Study, Gastroenterology, 2018, 154(6):S-481-S482.
Peery, et al., Practice Patterns for the Evaluation and Treatment of Eosinophilic Oesophagitis, Alimentary Pharmacology and Therapeutics, 2010, 32:1373-1382.
Pritchett, et al., Efficacy of Esophageal Impedance/pH Monitoring in Patients With Refractory Gastroesophageal Reflux Disease, On and Off Therapy, Clinical Gastroenterology and Hepatology, 2009, 7:743-748.
Puhan, et al., A Randomized Trial of Ways to Describe Test Accuracy: The Effect on Physicians' Post-Test Probability Estimates, Annals of Internal Medicine, 2005, 143(3):184-189.
Richter, How to Manage Refactory GERD, Nature Clinical Practice Gastroenterology & Hepatology, 2007, 4(12):658-664.
Saffari, et al., Patchy Eosinophil Distributions in an Esophagectomy Specimen from a Patient with Eosinophilic Esophagitis: Implications for Endoscopic Biopsy, Journal of Allergy and Clinical Immunology, 2012, 130(3):798-800.
Safroneeva, et al., Symptoms Have Modest Accuracy in Detecting Endoscopic and Histologic Remission in Adults With Eosinophilic Esophagitis, Gastroenterology, 2016, 150:581-590.
Sontag, et al., The Medical Management of Reflux Esophagitis. Role of Antacids and Acid Inhibition, Gastroenterology Clinics of North America, 1990, 19(3):683-712.
Sox, et al., The Influence of Types of Decision Support on Physicians' Decision Making, Archives of Disease in Childhood, 2009, 94(3):185-190.
Tobey, et al., Dilated Intercellular Spaces: A Morphological Feature of Acid Reflux-Damaged Human Esophageal Epithelium, Gastroenterology, 1996, 111:1200-1205.
Tutuian, et al., Gastroesophageal Reflux Monitoring: pH and Impedance, Goyal & Shaker GI Motility Online, 2006, http://www.nature.com/gimo/contents/pt1/full/gimo31.html, 12 pages.
Tutuian, et al. Rumination Documented by Using Combined Multichannel Intraluminal Impedance and Manometry, Abstract, Clinical Gastroenterology and Hepatology, 2004, 2(4):340-343, http://www.cghjournal.org/article/S1542-3565(04)00065-5/abstract, 2 pages.
Vaezi, et al.. Assessing Old and New Diagnostic Tests for Gastroesophageal Reflux Disease, Gastroenterology, 2018, 154(2):289-301.
Veerappan, et al., Prevalence of Eosinophilic Esophagitis in an Adult Population Undergoing Upper Endoscopy: A Prospective Study, Clinical Gastroenterology and Hepatology, 2009, 7:420-426.
Wenner, et al., Optimal Thresholds and Discriminatory Power of 48-h Wireless Esophageal pH Monitoring in the Diagnosis of GERD, American Journal of Gastroenterology, 2007, 102(9):1862-1869.
Woodland, et al., In Vivo Evaluation of Acid-Induced Changes in Oesophageal Mucosa Integrity and Sensitivity in Non-Erosive Reflux Disease, Gut, 2013, 62(9):1256-1261.

\* cited by examiner

SYSTEM AND METHOD FOR DETECTING AND MEASURING THE CONDITION OF INTRALUMINAL ESOPHAGEAL MUCOSA

CROSS-REFERENCE TO RELATED APPLICATIONS

This application claims the benefit of U.S. Provisional Patent Application No. 62/679,604 filed Jun. 1, 2018, and U.S. Provisional Patent Application No. 62/725,070 filed Aug. 30, 2018. The contents of each application are hereby incorporated by reference for all purposes as if set forth in their entirety herein.

BACKGROUND

Gastroesophageal reflux disease (GERD) is the leading outpatient physician diagnosis for gastrointestinal disorders in the United States affecting approximately 18-27% of the population. Despite the high prevalence and projected national expenditures ranging from $9.3 to $12.1 billion, our diagnostic armamentarium has largely remained static since initial development of intraluminal esophageal probes in the 1970s. Testing for GERD have primarily relied on endoscopic findings of mucosal damage (esophagitis) or demonstration of abnormal esophageal acid exposure detected by ambulatory pH or intraluminal impedance monitoring. However, it is well known that transnasal catheter-based testing is associated with significant patient discomfort (nose pain, throat pain, cough, chest discomfort), which can lead to alteration in patient's daily activities (less likely to be active, more likely to skip meals, and have difficulty with swallowing) leading to variable sensitivity of these tests.

This led to development of wireless pH monitoring technology, which allowed for prolonged monitoring and less patient discomfort, however, it only measured the acidity of refluxed material and can be subject to early detachment in 10% of examinations leading to extra cost burden of repeat testing and more importantly, delay in diagnosis for the patient. Furthermore, these tests fail to account for day to day variability of reflux as they only provide 24 to 48 hour "snap shot" of a disease process that is chronic in nature. Thus, even wireless pH monitoring, which is currently considered the most sensitive test for GERD and used to rule out reflux in proton pump inhibitor (PPI) refractory patients has false negative rate of nearly 30% in patients that have endoscopic esophagitis.

Eosinophilic esophagitis (EoE) is another esophageal disease that is increasing in prevalence and estimated to affect 57 per 100,000. EoE is an chronic immune mediated disease characterized by symptoms of esophageal dysfunction and histologically by eosinophil-predominant inflammation in the esophagus. Diagnosis is made using endoscopy and distal and proximal esophageal biopsies showing at least 15 eosinophils per high-power field (HpF). Due to need for esophageal biopsy for diagnosis and multiple endoscopies to document treatment response, the estimated median cost associated with EoE is approximately $2,302/year/patient, (See Jensen E T, et. al., *American Journal of Gastroenterol* 2015; 110:626-32). There is also significant overlay between GERD and EoE, with both often in the differential especially for young patients with dysphagia, which can lead to separate testing for each to determine the etiology. In addition, there is also significant overlap between clinical presentation of GERD and EoE with heartburn reported in 30-60% of patients with EoE. The overlap in symptoms can make clinical separation between GERD and EoE challenging prior to diagnostic testing given both are frequently in the differential.

Furthermore, EoE can be a patchy disease and while there are general recommendations on where to obtain biopsies to diagnose EoE (proximal and distal esophagus), one study showed that only 24% of academic and 3% of community gastroenterologists follow consensus guidelines to diagnose EoE, (See, Peery A F, et. al., *Ailiment Pharmacol. Ther.* 2010; 32:1373-82). This has also led to significant variability in diagnostic criteria used by studies for EoE in the literature ranging from 5 to 30 eosinophils/HpF with large proportion of studies (35%) not even stating their diagnostic criteria. (See, Dellon E S, et. al., Am. J. Gastroenterol, 2007; 102:2300-13). Levels of esophageal eosinophilia has also been shown to vary widely throughout locations in the esophagus and even within biopsies themselves. Thus, there is no way to ensure that biopsies taken will not miss a diagnosis of EoE. Overlap among clinical presentations between GERD and EoE along with inadequate reliability of endoscopic features and histopathological changes can make it challenging for a clinician to reliably choose the correct diagnostic test.

Currently, there is a need in the art for the development of diagnostic tools that can assist clinicians to differentiate esophageal conditions, such as GERD from EoE or other esophageal conditions that present similar symptoms. The development of such tools would decrease the rate of misdiagnosis, reduce testing and procedure costs, thereby saving money in healthcare spending.

SUMMARY

Disclosed are catheter systems and methods of using the catheter system to acquire mucosal impedance data of a patient. Also disclosed are methods of classifying or otherwise identifying esophageal conditions in a subject based on mucosal impedance data acquired using a catheter system. Unlike conventions systems that require subjective input from a physician to render a diagnosis, the systems and methods described herein can utilize the mucosal impedance measurements to generate a probability that the subject's esophagus corresponds to an esophageal condition or a set of esophageal conditions. In one embodiment, a classification model is used to generate the probability. The classification model may generate the probability based at least in part on a change in the mucosal impedance measurements between a distal location and a proximal location on the subject's esophagus.

Some embodiments of the present disclosure provide a catheter system that includes a catheter having an elongate shaft extending between a proximal end and a distal end, a plurality of impedance sensing electrodes configured between the proximal end and the distal end, and an inflatable and deflatable balloon configured to the elongate shaft of the catheter. The catheter system further includes a computer system communicatively coupled to the catheter, and wherein the computer system is programmed to control the inflatable and deflatable balloon to expand to place at least a portion of the impedance sensing electrodes in contact with an esophageal mucosa on the interior esophageal wall of a subject. The computer system is further programmed to acquire mucosal impedance data of the esophageal mucosa at a plurality of axial positions between the distal position and the proximal position of the catheter by directing an electric current through the esophageal mucosa via the impedance sensing electrodes, and generate a report that includes a probability that at least a portion of the subject's esophageal mucosa corresponds to one or more esophageal condition, wherein the probability is generated based at least in part on the mucosal impedance data acquired between the proximal end and the distal end of the catheter.

In further embodiments, the computer system is further programmed to generate a probability that the esophageal mucosa corresponds to a set of esophageal conditions, where the probability is generated based at least in part on the musical impedance data acquired between the proximal end and the distal end of the catheter. The set of esophageal conditions may include gastroesophageal reflux disease (GERD), eosinophilic esophagitis (EoE), and non-gastroesophageal reflux disease (NERD), among others.

In some embodiments, the computer system is further programmed to utilize a classification model to generate the probability based on one or more input parameter, wherein the one or more input parameter includes a change of mucosal impedance between two or more axial positions configured between the proximal end and the distal end of the catheter. The classification model may comprise a multinomial logistic regression, where the multinomial logistic regression generates the probability based at least in part on fitting the mucosal impedance data at two or more of the axial positions to generate a classification slope and a classification intercept, and generating the probability using the classification slope and the classification intercept.

In further embodiments, the exterior surface of the catheter includes at least two impedance sensing electrodes at a plurality of axial positions along the length of the catheter.

In some embodiments, the computer system is further programmed to identify and remove non-contact impedance data from the acquired mucosal impedance data to generate corrected mucosal impedance data. The non-contact impedance data corresponds to impedance data generated when the impedance sensing electrodes are in contact with a remnant in the subject's esophagus that is different than the esophageal mucosa, and wherein the computer system identifies and removes the non-contact impedance data if the data corresponds to one or more of the following conditions: (a.) acquired impedance data that exceeds a threshold impedance measurement, wherein the threshold measurement is 5000 Ohms; and (b.) acquired impedance data that has a studentized residual above 3.

In further embodiments, the computer system is further programmed to store an individual correction factor for at least a portion of the impedance sensing electrodes in a memory of the computer system, and generate corrected mucosal impedance data by applying the individual correction factor to the mucosal impedance data acquired by the corresponding impedance sensing electrode.

In some embodiments, the computer system is further programmed to generate the individual correction factors by calibrating at least a portion of the impedance sensing electrodes using a saline solution having a known impedance and concentration.

In further embodiments, a catheter system is provided that includes a catheter including an elongate shaft extending between a proximal end and a distal end, a plurality of impedance sensing electrodes configured between the proximal end and the distal end, an inflatable and deflatable balloon configured to the elongate shaft. The catheter system further includes a computer system communicatively coupled to the catheter, and where the computer system is programmed to control the inflatable and deflatable balloon to expand to place at least a portion of the impedance sensing electrodes in contact with an esophageal mucosa on the interior esophageal wall of a subject. The computer system is further programmed to acquire mucosal impedance data of the esophageal mucosa at a plurality of axial positions between the distal position and the proximal position of the catheter by directing an electric current through the esophageal mucosa via the impedance sensing electrodes, and generate corrected mucosal impedance data by identifying and removing non-contact impedance data from the acquired mucosal impedance data to generate corrected mucosal impedance data, wherein the non-contact impedance data corresponds to impedance data generated when the impedance sensing electrodes are in contact with a remnant in the subject's esophagus that is different than the esophageal mucosa. The computer system is further programmed to generate a report that includes a probability that at least a portion of the subject's esophageal mucosa corresponds to one or more esophageal condition, wherein the probability is generated based at least in part on a change in the corrected mucosal impedance data between the proximal end and the distal end of the catheter.

In some embodiments, the computer system is further programmed to generate a probability that the esophageal mucosa corresponds to a set of esophageal conditions, wherein the probability is generated based at least in part on the musical impedance data acquired between the proximal end and the distal end of the catheter. In some embodiments, the set of esophageal conditions includes gastroesophageal reflux disease (GERD), eosinophilic esophagitis (EoE), and non-gastroesophageal reflux disease (NERD).

In further embodiments, the computer system is further programmed to utilize a classification model to generate the probability based on one or more input parameter, wherein the one or more input parameter includes a change of mucosal impedance between two or more axial positions configured between the proximal end and the distal end of the catheter. In some embodiments, the classification model comprises a multinomial logistic regression, where the multinomial logistic regression generates the probability based at least in part on fitting the mucosal impedance data at two or more of the axial positions to generate a classification slope and a classification intercept, and generating the probability using the classification slope and the classification intercept.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
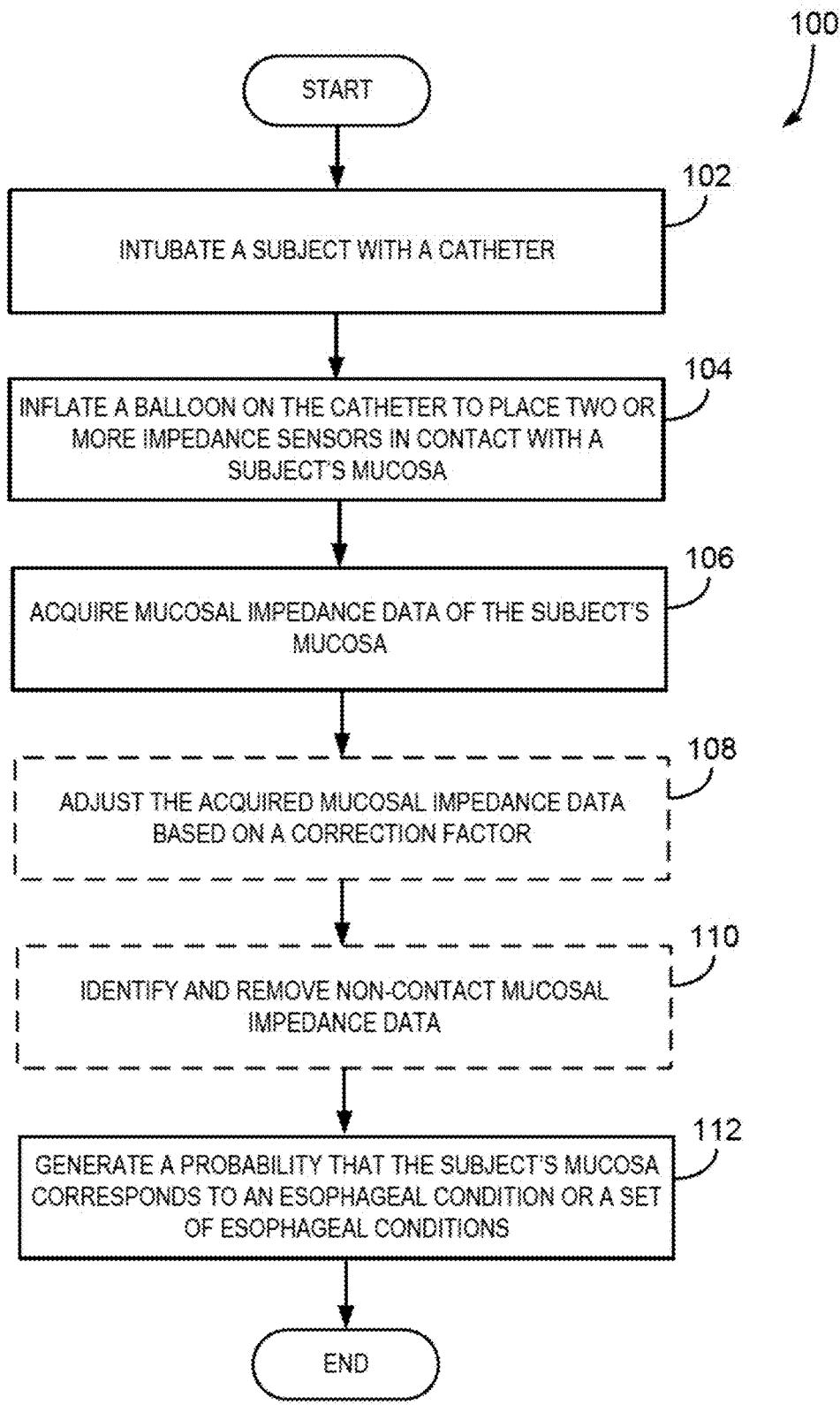
FIG. 1 is a flowchart setting forth the steps of a method for acquiring esophageal mucosal impedance data in accordance with an embodiment described in the present disclosure.

Described herein are systems and methods for classifying, identifying, or otherwise measuring parameters indicative of esophageal conditions in a subject. In general, the methods of the present disclosure include first acquiring mucosal impedance measurements along the length of a subject's esophagus, and then utilizing the mucosal impedance measurements to generate a probability that the subject's esophagus corresponds to an esophageal condition or a set of esophageal conditions. In one embodiment, a classification model is used to generate the probability. The classification model may generate the probability based at least in part on a change in the mucosal impedance measurements between a distal location and a proximal location on the subject's esophagus.

As used herein, the term "esophageal condition" may refer to any disease state, syndrome, or disorder corresponding to a portion of a patient's esophagus. Exemplary esophageal conditions include, but are not limited to gastroesophageal reflux disease (GERD), nonerosive reflux disease (NERD), Barrett's esophagus, and esophagitis conditions, such as eosinophilic esophagitis (EoE). Often times, clinical features cannot be relied on to distinguish between esophageal conditions. This can be attributed to the fact that many esophageal conditions present with similar, if not the same, clinical symptoms. For example, it is not uncommon for a patient with the aforementioned esophageal conditions to report symptoms such as heartburn and acid regurgitation. However, heartburn and acid regurgitation are ubiquitous to most esophageal conditions. Further, many esophageal conditions present with similar visual symptoms (e.g., redness and inflammation of mucosa), making endoscopy often inconclusive. Thus, distinguishing between esophageal conditions is a non-trivial task, and physicians often rely on diagnostic tools to help correctly diagnose the condition based on the underlying pathophysiology of the mucosa and responses to previous treatments, such as proton pump inhibitors (PPI) and other acid suppressing agents.

In some embodiments, the term "GERD" may be characterized as a chronic condition that develops when the reflux of gastric contents spills into the esophagus in significant quantities to cause troublesome symptoms with or without mucosal erosions and/or relevant complications. The term "NERD" may be characterized as a condition that presents with troublesome reflux-related symptoms in the absence of esophageal erosions and/or breaks (e.g., dilated intercellular spaces) at conventional endoscopy and without recent acid-suppressive therapy. The term "Barrett's esophagus" may be characterized as a change in the esophageal mucosa at any length that is confirmed to have esophageal erosions and/or breaks. Conventionally, the erosions and/or breaks are confirmed by biopsy and may be recognized at endoscopy. Treatments for the aforementioned esophageal conditions typically include administering proton pump inhibitors (PPI) and acid suppressing agents, while in advanced cases, treatment may require surgery. The term "EoE" may be characterized by a dense esophageal eosinophilia with severe squamous epithelial hyperplasia, where the esophageal abnormalities do not respond to treatment with high-dose proton pump inhibitor (PPI) therapy. Treatment for EoE typically includes dietary approaches based on eliminating exposure to allergens, such as food or corticosteroids. Given that many esophageal conditions present with similar conditions but may require different treatment options, it is important that physicians have effective diagnostic tools to assist in making the proper diagnosis.

As stated above, conventional diagnostic tools (e.g., pH monitoring and biopsies) for diagnosing esophageal conditions are limited and often time intensive. For example, tools for diagnosing GERD primarily consist of pH monitoring (catheter or wireless) or non-contact, multi-channel intraluminal impedance/pH monitoring, which are limited to detection of only intraluminal reflux events over 24- to 48-hour periods, and thus, only provide a "snapshot" measure of a chronic disease process. On the other side, diagnosis for EoE has relied on obtaining distal and proximal esophageal biopsies and histopathological confirmation, which can lead to added cost burden and delay of treatment and diagnosis.

Unlike conventional methods, mucosal impedance (MI) catheters provide a new paradigm for characterizing the condition of esophageal mucosa. Mucosal impedance catheters provide fast (e.g., on the order of minutes or seconds), accurate, and direct measurement of physiological signals corresponding to a patient's esophagus (e.g., conductivity and impedance) that may be used to track histological changes. Direct physiological signals acquired from a patient's mucosa can provide a great deal of information about the patient's mucosal tissue properties and the pathological condition of the mucosa. DIS is typically defined by the space or distance between esophageal epithelial cells and is regulated by tight junction proteins. In general, a high degree of DIS is typically a characteristic of damaged mucosa.

Damaged mucosa may result from exposure of the esophageal mucosa to acidic fluids, e.g., gastric acid and digestive enzymes from the stomach for abnormal times or at abnormal levels, which depending on the exposure time and intensity may manifest in varying degrees of mucosal damage. Milder damage levels are not detectable with routine visual endoscopic examination, while more advanced damage is endoscopically visible as varying degrees of esophagitis or Barrett's esophagus. As mucosa become damaged the dilated intracellular spaces provide greater access of luminal refluxate H+ ions to nociceptors within the esophageal mucosa, thereby serving as a basis for enhanced chemoreceptor perception of refluxate, thus pain. The esophageal epithelium of a healthy esophagus provides a structural barrier, which resists the diffusion of refluxed and ingested materials through the mucosa. Abnormal exposure of the esophageal epithelium to reflux of acid, pepsin, and bile from the stomach can result in damage to the cellular junction complex of the esophageal epithelium. The increased salt and water flow allowed by these compromised cellular junctions result in further damage and the eventual development of dilated intracellular spaces in the epithelium.

In patients with DIS, the potential difference changes for esophageal mucosa having varying degrees of DIS across the esophagus. Esophageal epithelium having higher degrees of DIS will have higher acid perfusion and will reflect elevated ion permeability in the mucosa and a lower impedance. Various esophageal conditions have varying degrees of dilated intracellular spaces in the epithelium and demonstrate unique mucosal impedance patterns along the esophagus. For example, patients having GERD typically have lower mucosal impedance values near the squamocolumar junction (SCJ) and increase in the mid and proximal esophagus, while patients with EoE have low mucosal impedance values along the esophagus. However, trends between esophageal conditions may not always be immediately discernable. For example, depending on the degree of DIS across the esophagus, there may be circumstances where two or more viable diagnostic options for the esophageal condition exist. To address the aforementioned problems, the present disclosure provides a catheter system and methods for acquiring mucosal impedance data that may be used to generate a probability corresponding to the likelihood that a patient's mucosa is associated with an esophageal condition or a set of esophageal conditions.

Figure 2:
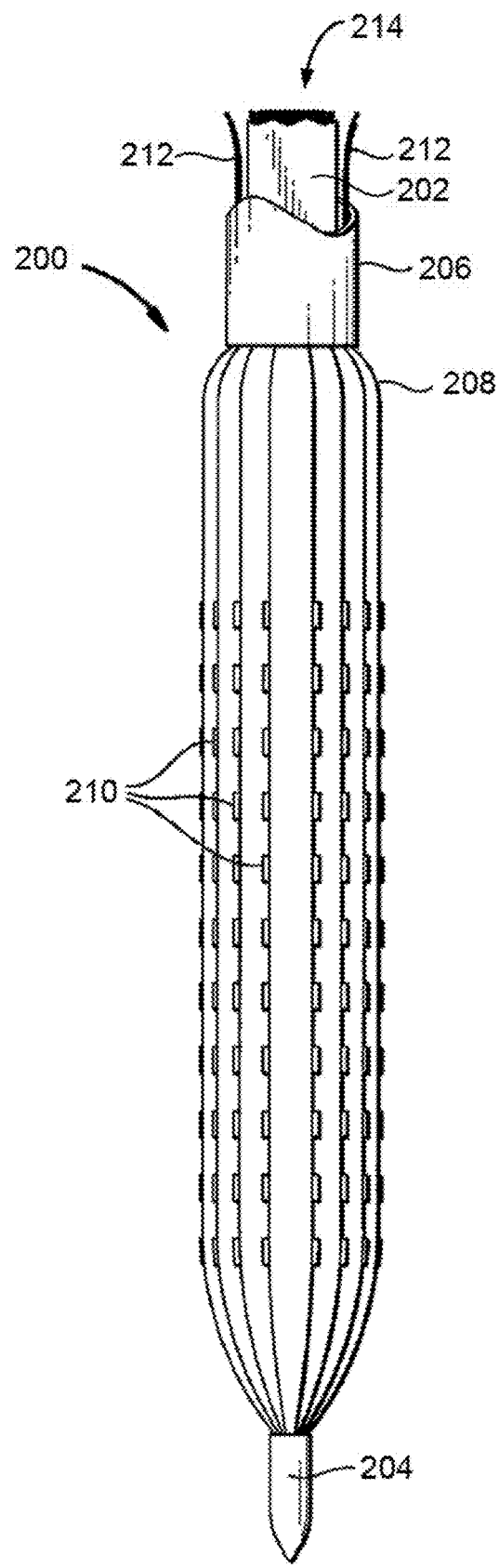
FIG. 2 is an exemplary catheter in accordance with an embodiment described in the present disclosure.

Overview of Methods:

Referring now to FIG. 1, a flowchart is provided as setting forth the steps of an example method 100 for identifying an esophageal condition in a subject using a catheter system. The method 100 includes intubating a subject with a catheter, as indicated by process block 102. An example catheter 200 for use in the methods presented herein is illustrated in FIG. 2. In some embodiments, the catheter 200 includes an elongate shaft 202 that extends between a distal end 204 and a proximal end 206, an inflatable and deflatable balloon 208, and impedance sensing electrodes 210 positioned between the distal end 204 and the proximal end 206. In some embodiments, intubating the subject with the catheter 200 may include positioning the distal end 204 of the catheter to be in contact with the lower esophageal sphincter (LES) of the subject. A pressure sensor (not shown) may be configured to the distal end 204 of the catheter 200 to assist in the detection of the LES. For example, the LES may be detected by pushing the distal end 204 of the catheter 200 through the LES and into the subject's stomach, whereupon the pressure will fall as the distal end 204 of the catheter 200 enters the cavity of the stomach. The catheter 200 may then be pulled up until the pressure rises, which provides an indication that the distal end 204 of the catheter 200 is in contact with the LES. In alternative embodiments, the catheter 200 may be intubated such that the distal end 204 of the catheter 200 is positioned at any length within the subject's esophagus. For example, the distal end 204 of the catheter 200 may be initially placed in contact with the LES and subsequently pulled upwards at a distance relative to the LES, such as 1 cm, or 2 cm, or 3 cm, or 4 cm, or 5 cm, or 6 cm, or 7 cm, or 8 cm, or 9 cm, or 10 cm above the LES.

Following intubation, the method 100 includes inflating the balloon 208 to place at least a portion of the impedance sensing electrodes 210 in contact with the subject's esophageal mucosa, as indicated by process block 104. The balloon 208 may be controllably inflated using fluid from a pressurized fluid supply tank, such as a tank filled with gas (e.g., air) or fluid (e.g., water). The elongate shaft 202 in the catheter 200 may include a channel 214 that places the pressurized fluid supply tank in fluid communication with the inflatable and deflatable balloon 208. The rate of inflation and deflation may be safely controlled using one or more valves (not shown) positioned between the fluid supply tank and the inflatable and deflatable balloon 208. In some aspects, the values are controlled manually or with a processor in a computer system to regulate the flow. In some embodiments, the impedance sensing electrodes 210 are spaced axially along the elongate shaft 202 or on an exterior surface of the balloon 208 of the catheter 200, and may include one or more impedance sensing electrode 210 at each axial location. Having two or more impedance sensing electrodes 210 at each axial position may improve measurement accuracy, as single channel mucosal impedance catheters may be subject to inter-provider variability due to lack of adequate contact with mucosa from catheter movement and intraluminal gas and fluid (e.g., in the case of a 360 degree design impedance sensor). In some embodiments, two or more impedance sensor electrodes are position at each axial position, where the impedance sensor electrodes are positioned at 90 degrees or 180 degrees relative to each other on the catheter surface. Other suitable mucosal impedance sensor catheter configurations have been previously described, for example, in U.S. patent application Ser. No. 13/182,417, which is incorporated herein by reference.

After the impedance sensing electrodes 210 are placed in contact with the mucosa, mucosal impedance data are acquired by directing an electric current through the esophageal mucosa of the subject via the impedance sensing electrodes 210 and measuring the impedance of the mucosa, as indicated by process block 106. In some embodiments, the current is provided to the impedance sensing electrodes 210 via wires 212. The wires 212 may be placed in electrical communication with a processor that regulates the applied current, and is further configured to receive and process the mucosal impedance data.

Acquisition of the mucosal impedance data 106 may be performed in a number of ways. For example, the mucosal impedance data may be acquired 106 using a single acquisition or by using multiple acquisitions. In one embodiment, the impedance sensing electrodes 210 are controlled to acquire mucosal impedance data 106 at a plurality of axial and radial positions along the length of the subject's esophagus in a single acquisition. Alternatively, a single acquisition may be performed to acquire mucosal impedance data 106 along a single channel of impedance sensing electrodes 210. In some embodiments, a single channel may be defined by a column of impedance sensing electrodes 210 on the catheter 200. In some embodiments, a single acquisition may be performed to acquire the mucosal impedance data 106 at a single axial position on the catheter 200. The single axial position may be defined by a row of impedance sensing electrodes 210 on the catheter 200. In some embodiments, the number of impedance sensing electrodes 210 and position of impedance sensing electrodes that are acquiring mucosal impedance data may be controlled by a processor in electrical communication with the catheter 200.

In another embodiment, multiple acquisitions are used to acquire the mucosal impedance data 106. For example, acquiring the mucosal impedance data 106 using multiple acquisitions may include positioning the impedance sensing electrodes 210 in a first position along the length of the subject's esophagus, and acquiring a first set of mucosal impedance data. The impedance sensing electrodes 210 are then repositioned to a second position in the subject's esophagus (e.g., moved radially and/or axially), and the impedance sensing electrodes 210 are controlled to acquire mucosal impedance data at the second position. In one non-limiting example, a first set of mucosal impedance data may be acquired by positioning the distal end 204 of the catheter 200 in the LES of the subject. A second set of mucosal impedance data may then be acquired by pulling the catheter 200 upwards to a second position, and acquiring the mucosal impedance data at the second position. This process may be repeated to acquire multiple axial and/or radial impedance measurements along the length of the subject's esophagus. In one embodiment, the multiple acquisitions are acquired by incrementally pulling the catheter 200 along the length of the patient's esophagus. Incrementally pulling the catheter 200 may include pulling the catheter at evenly spaced axial distances or at randomly varied distances, and may be performed manually or through the assistance of an actuator. In one non-limiting example, the actuator comprises a spool and motor that is configured to controllably pull the elongate shaft 212 of the catheter 200. The actuator may be controlled using the processor to move the catheter 200 at fixed or random distances. Spatial data may be recorded by the processor. For example, the spatial data may include the impedance sensing electrodes 210 distance from the LES or squamocolumnar junction (SCJ), which may be used to map or record impedance data along the subject's esophagus.

Referring back to FIG. 1, the method 100 further includes generating a probability that the subject's esophageal mucosa corresponds to an esophageal condition or a set of esophageal conditions based at least in part on the acquired mucosal impedance data, as indicated by step 112. As described above, various esophageal conditions elicit unique impedance patterns along the length of the esophagus that may be indicative of a particular esophageal condition. In one embodiment, the probability is generated using a classification model. Suitable classification models may be used to assign or generate a probability that the unique impedance patterns along the subject's esophagus correspond to an esophageal condition or a set of esophageal conditions. The classification model may generate the probability based on one or more input parameters. One suitable input parameter may include the change in mucosal impedance between a proximal and distal position along the length of the subject's esophagus. Other suitable input parameters may include, but are not limited to, esophageal pH (e.g., pH as a function of esophageal position or average esophageal pH), esophageal color (e.g., obtained from endoscopy), mucosa tissue pathology (e.g., obtained from biopsy), laboratory tests (e.g., cholesterol levels, triglyceride levels), medical image data (e.g., x-ray, MRI, ultrasound), treatment history (e.g., medications), subject medical history (e.g., existing medical conditions), or any other data relied upon by a doctor to assist in making a diagnosis of the subject.

In one embodiment, the classification model is built from the acquired mucosal impedance data, for example, by fitting the impedance data to a multinomial logistic regression. For example, the classification model may be built by fitting the mucosal impedance data at two or more axial positions to generate a classification slope and a classification intercept. Once the classification model is built, the model may be applied to the mucosal impedance data to generate the probability that the subject's mucosa corresponds to an esophageal condition or a set of esophageal conditions. The classification model may be built simultaneously during the acquisition of mucosal impedance data, or may be pre-built based on previously acquired mucosal impedance data. In some aspects, building the model simultaneously during data acquisition yields improved accuracy of correctly predicting the esophageal condition.

In one embodiment, the probability is generated for a diagnostic group that includes a candidate set of esophageal conditions for analysis. The diagnostic group may include, for example, at least 10 candidate esophageal conditions, or at least 9 candidate esophageal conditions, or at least 8 candidate esophageal conditions, or at least 7 candidate esophageal conditions, or at least 6 candidate esophageal conditions, or at least 5 candidate esophageal conditions, or at least 4 candidate esophageal conditions, or at least 3 candidate esophageal conditions, or at least 2 candidate esophageal conditions. In one non-limiting example, the classification model may be applied to a diagnostic group that includes three candidate esophageal conditions, such as GERD, NERD, and EoE. Probabilities for each of the three candidate esophageal conditions may then be determined as a function of the change in mucosal impedance as a function of distance along the subject's esophagus. The change in mucosal impedance may be measured using the classification slope and a classification intercept. In one embodiment, the classification slope and classification intercept are generated using multinomial logistic regression.

Prior to the generation of the probabilities using the classification model, the candidate esophageal conditions in the diagnostic group may be assigned a baseline probability. In some aspects, the baseline probability may relate to the prevalence of each esophageal condition, or may be arbitrarily assigned. For example, the baseline probability for a diagnostic group including GERD, NERD, and EoE may initially be assigned to be 35%, 35%, 30%, respectively. Separate multivariable logistic regression models may be fit either using either GERD (vs EoE and non-GERD), EoE (versus GERD and non-GERD) or non-GERD (versus GERD and EoE) as the outcome of interest. Other suitable classification models include, but are not limited to, decision tree classifiers, rule-based classifiers, neural networks, support vector machines, non-linear classification models, and linear classification models.

Figure 3:
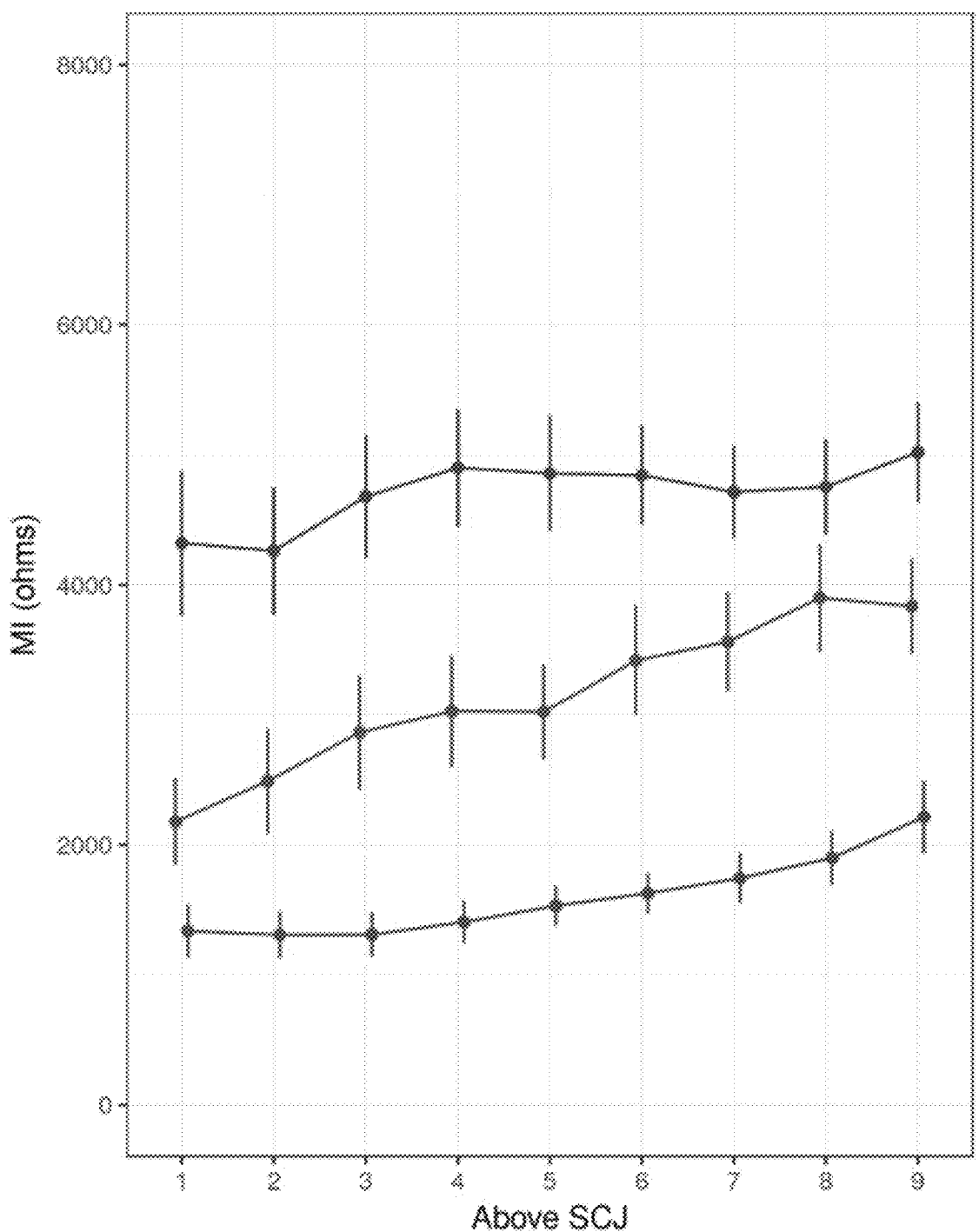
FIG. 3 is a graphical illustration of exemplary mucosal impedance (MI) data acquired using a catheter system in accordance with an embodiment described in the present disclosure.
Figure 4:
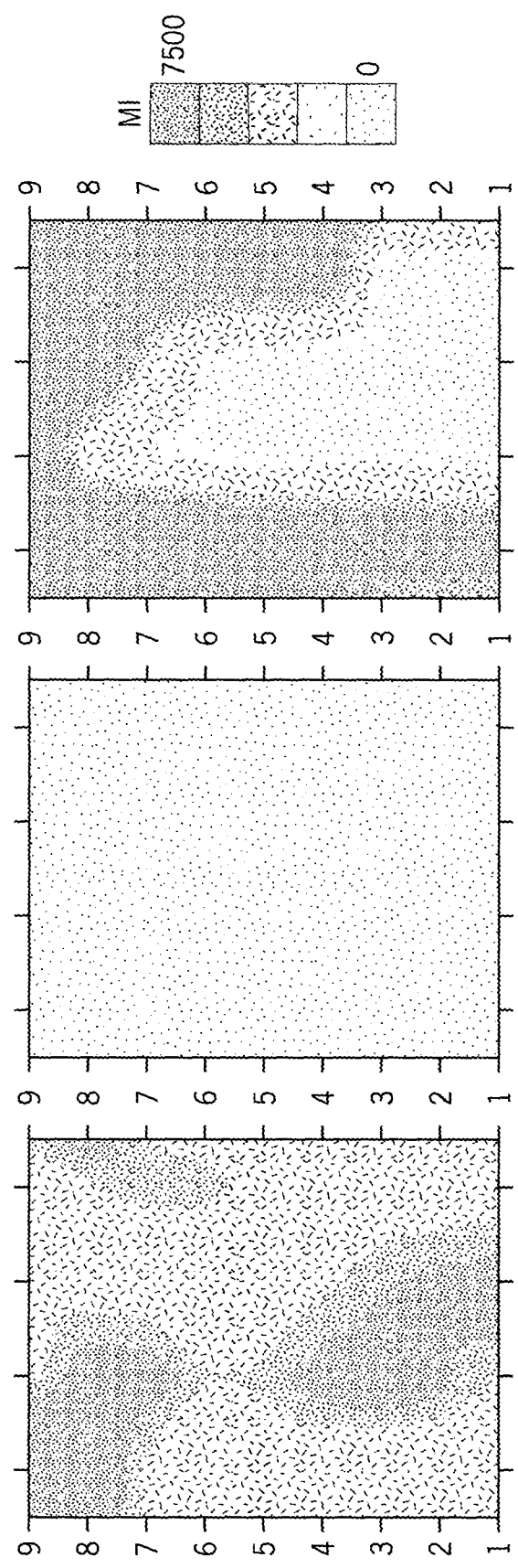
FIG. 4 is a graphical illustration of three contour plots including exemplary mucosal impedance data acquired using a catheter system in accordance with an embodiment described in the present disclosure.

In some embodiments, the method 100 further includes displaying the mucosal impedance data and/or the probability that subject's mucosa corresponds to an esophageal condition or a set of esophageal conditions. The probability results may be generated and displayed simultaneously with data acquisition. Alternatively, previously acquired mucosal impedance data may be provided to a computer system to generate the probability using the classification model. Subsequently, the probability may be displayed in a number of ways, for example, in a report and/or graphically. Suitable graphs include two dimensional or three dimensional graphs, including, but not limited to, bar graphs, line graphs, contour plots, iso-contour plots, etc., and they can be represented in colors for various values or features. FIG. 3 is a non-limiting example of a line graph that includes a display of the acquired mucosal impedance data as a function of the number of impedance sensors above the SCJ. FIG. 4 is a non-limiting example of a contour plot that displays the acquired mucosal impedance as a function of distance from the SCJ. The catheter in FIG. 4 includes four mucosal impedance sensors configured at each axial position along the catheter.

Figure 5:
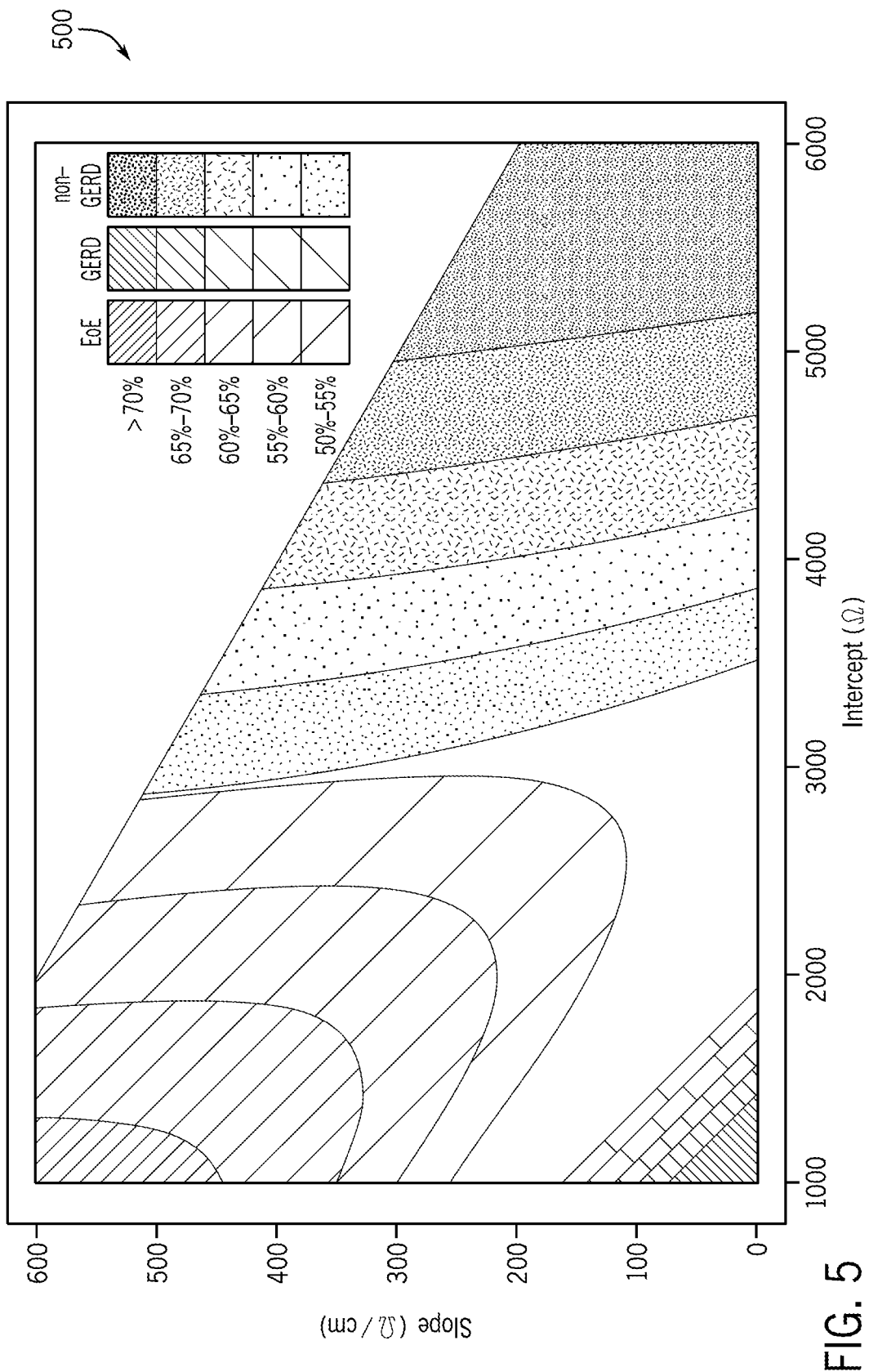
FIG. 5 is a graphical illustration of a probably heat map generated from a classification model in accordance with an embodiment described in the present disclosure.

Referring to FIG. 5, a non-limiting example of a graph 500 is illustrated in accordance with the present disclosure. The graph 500 includes a probability heat map generated from a classification model. In one embodiment, the graph 500 includes the probability that the subject's esophageal mucosa corresponds to an esophageal condition and, in this particular example, is generated based on the change in mucosal impedance as a function of distance along the subject's esophagus. Once generated, the probability heat map may be used to determine a probability that a subject's mucosa corresponds to an esophageal condition. For example, FIG. 5 illustrates that a patient with no rise in MI measurements from distal to proximal esophagus (slope of approximately zero) and an intercept (measurement at 1 cm from SCJ) of 1000Ω would have 82% probability of having EoE compared to 13% probability of GERD and 5% probability of being non-GERD. On the other hand, a patient with an intercept of 1000Ω, but a rapid rise in MI measurements from distal to proximal esophagus (slope of 600Ω) would have 67% probability of having GERD, 31% probability of being non-GERD, and 2% probability of EoE.

Figure 6:
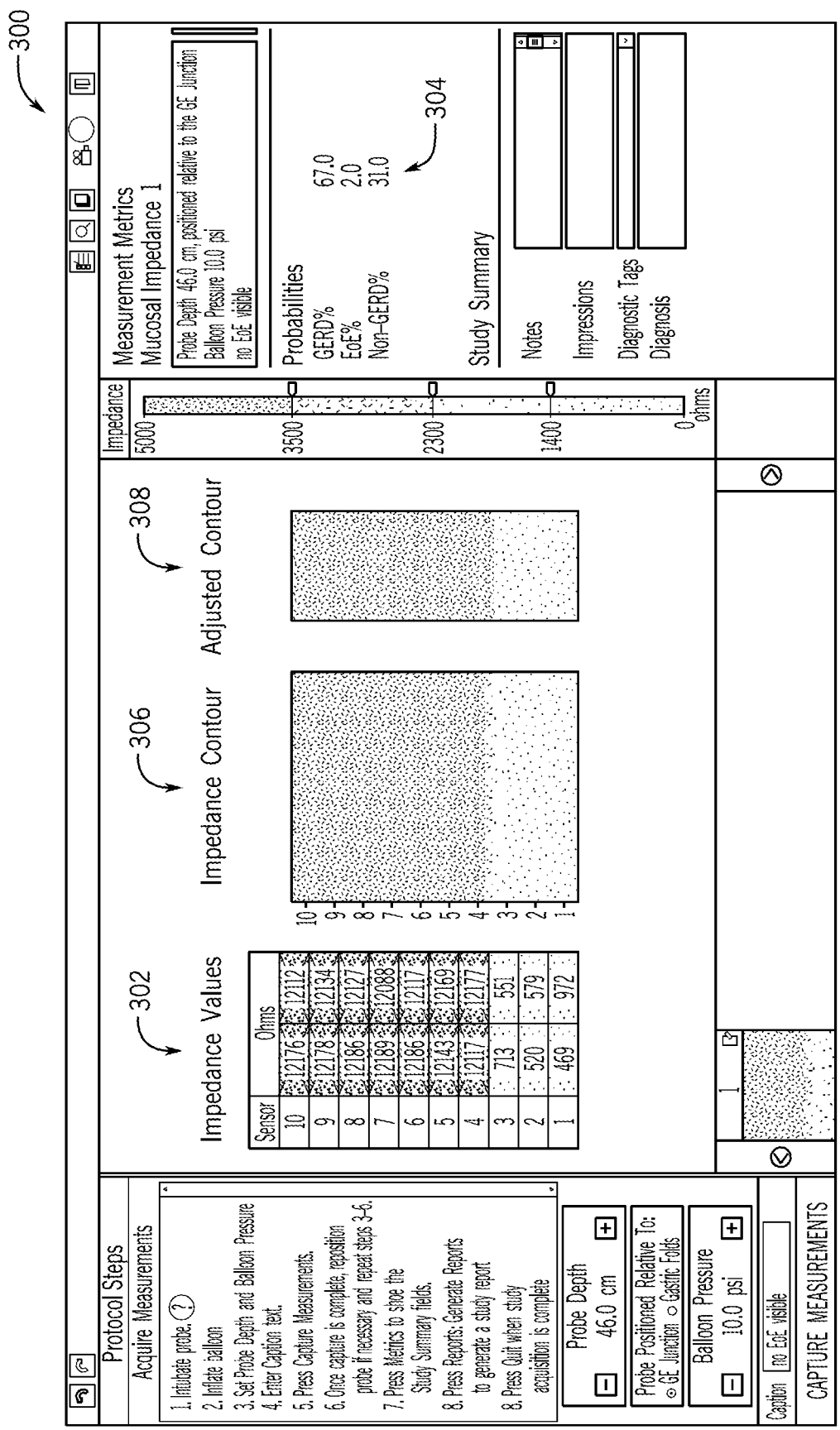
FIG. 6 is an exemplary report generated using a catheter system in accordance with an embodiment described in the present disclosure.

Referring to FIG. 6, a non-limiting example of a report 300 is illustrated in accordance with the present disclosure. In one embodiment, the report 300 includes a probability 304 indicating the likelihood that the subject's esophageal mucosa corresponds to one or more esophageal condition. In this particular example, the report includes probabilities for a set of three esophageal conditions comprising GERD, EoE, and NERD. In some embodiments, the report 300 further displays the acquired mucosal impedance data that may be presented, for example, in tabular form 302 or as a contour map 306.

Referring back to FIG. 1, the method 100 may further include an optional processing step 108 to adjust the acquired mucosal impedance data based on a correction factor to generate corrected mucosal impedance data. Often times, at the time of manufacture, impedance sensing electrodes have slight defects or minor contaminations on the surface of the electrode that may attribute to impedance variability between each electrode. In some instances, the variability of impedance between each of the impedance sensing electrodes is significant in affecting the accuracy of identifying the esophageal condition. To accommodate for the variability between the electrodes, a correction factor may be applied to one or more of the impedance sensing electrodes on the catheter 200 to reduce or eliminate inter-electrode impedance variability. In one embodiment, the correction factor is determined based on calibrating the impedance sensing electrode to a saline solution having a known concentration and impedance. Suitable saline solutions may comprise one or more salt, such as sodium chloride. In some embodiments, individual correction factors for one or more impedance sensing electrode are stored in a cache memory of a computer system in electrical communication with the catheter 200. Correction factors may be applied to the mucosal impedance data acquired by the corresponding impedance sensing electrodes. Applying the correction factor may reduce or eliminate inter-electrode impedance variability improves the accuracy of identifying the esophageal condition.

In some embodiments, the method 100 may further include an optional processing step 110 to identify impedance measurements that do not contact the esophageal mucosa, and to remove the non-contact impedance data to generate corrected mucosal impedance data. In some aspects, it may be possible that the impedance sensing electrodes 210 do not adequately contact the esophageal mucosa during inflation of the balloon 208. Inadequate contact may be attributed to, at least in part, improper positioning of the catheter during intubation. Exemplary non-contact impedance measurements include remnants in the esophageal pathway (e.g., food and/or liquid) and gases (e.g., air and/or refluxate). Other exemplary non-contact impedance measurements may include faulty sensors that do not produce an impedance measurement (e.g., broken sensor). In most instances, remnants have impedance measurements that differ significantly from mucosal impedance measurements, and if the non-contact impedance measurements are included in the classification model, the accuracy of correctly identifying the esophageal condition may be reduced. As one example, air has an impedance measurement that is significantly greater than the impedance of esophageal mucosa. If the air impedance measurements are included in the classification model then the data may be biased or skewed away from the true measured values. In one embodiment, non-contact impedance measurements may be identified and removed if the impedance data exceeds a pre-determined threshold, such as impedance measurements that are greater than 5,000 Ohms, or greater than 5,500 Ohms, or greater than 6,000 Ohms, or greater than 6,500 Ohms, or greater than 7,000 Ohms, or greater than 7,500 Ohms, or greater than 8,000 Ohms, or greater than 8,500 Ohms, or greater than 9,000 Ohms, or greater than 10,000 Ohms, or more. Alternatively or additionally, non-contact impedance measurements may be identified and removed if the impedance measurement has a studentized residual above a threshold relative to adjacent axial or longitudinal measurements, such as a studentized of between 3 to 3.5.

In one embodiment, corrected mucosal impedance data may be generated using optional process step 108 and/or 110. As shown in FIG. 6, the corrected mucosal impedance data may be used to generate an adjusted contour plot 308. In some aspects, generating the adjusted contour plot or corrected mucosal impedance data may also include averaging or taking the median of the acquired mucosal impedance data at one or more axial or longitudinal position.

Figure 7:
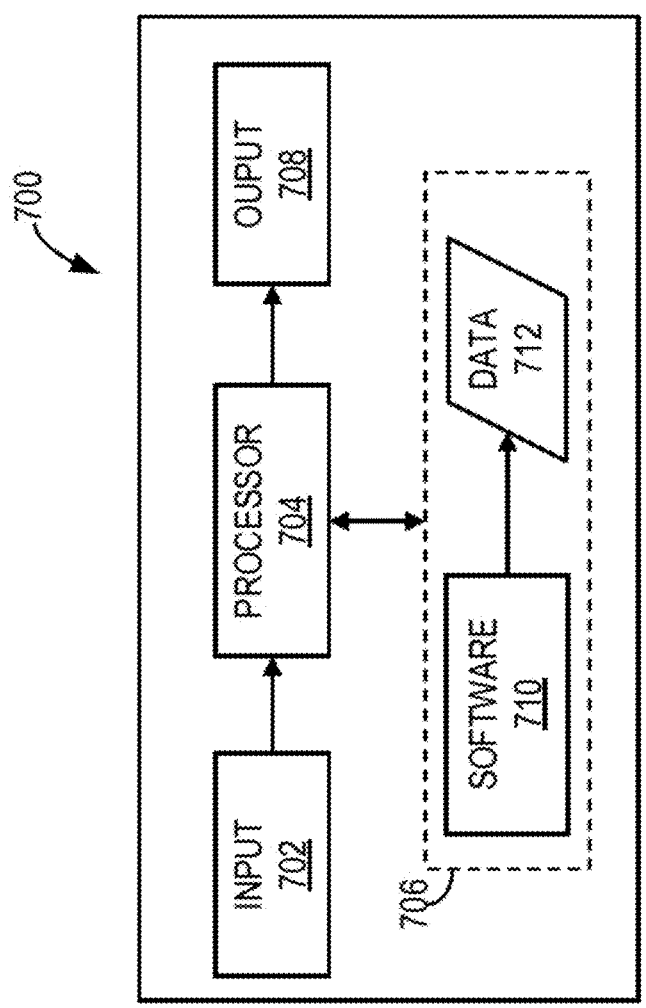
FIG. 7 is a block diagram illustrating an example of a computer system that can implement some of the embodiments of the present disclosure.

Referring now to FIG. 7, a block diagram of an example of a computer system 700 that can perform the methods described in the present disclosure is shown. The computer system 700 generally includes an input 702, at least one hardware processor 704, a memory 706, and an output 708. Thus, the computer system 700 is generally implemented with a hardware processor 704 and a memory 706. In some embodiments, the computer system 700 can be implemented, in some examples, by a workstation, a notebook computer, a tablet device, a mobile device, a multimedia device, a network server, a mainframe, one or more controllers, one or more microcontrollers, or any other general-purpose or application-specific computing device.

The computer system 700 may operate autonomously or semi-autonomously, or may read executable software instructions from the memory 706 or a computer-readable medium (e.g., a hard drive, a CD-ROM, flash memory), or may receive instructions via the input 702 from a user, or any another source logically connected to a computer or device, such as another networked computer or server. Thus, in some embodiments, the computer system 700 can also include any suitable device for reading computer-readable storage media.

In general, the computer system 700 is programmed or otherwise configured to implement the methods and algorithms described in the present disclosure, such as those described in FIGS. 1-6. For instance, the computer system 700 can be programmed to identify an esophageal condition corresponding to a subject's esophageal mucosa. In one aspect, the computer system 700 can be programmed to generate a probability that a subject's esophageal mucosa corresponds to an esophageal condition or a set of esophageal conditions based at least in part on acquired mucosal impedance data along the length of the subject's esophagus. In some aspects, the computer system 700 may be programmed to access acquired mucosal impedance data from a catheter system, such as the catheter system described in FIG. 2 or FIG. 8. Alternatively, the acquired mucosal impedance data may be provided to the computer system by acquiring the data using a catheter system and communicating the acquired data to the computer system 700, which may be part of the catheter system in FIG. 2 or FIG. 8.

The computer system 700 may be further programmed to process the acquired mucosal impedance data to generate a probability that the subject's esophageal mucosa corresponds to an esophageal condition or a set of esophageal conditions. In one embodiment, the computer system 700 may use a classification model, such as a multinomial logistic regression, to generate the probability based at least on one or more input parameter, such as a change in mucosal impedance data along the length of the subject's esophagus. The computer system 700 may also be programmed to generate corrected mucosal impedance data. For example, the computer system 700 may be programmed to adjust the acquired mucosal impedance data based on a correction factor, identify and remove non-contact mucosal impedance data, and/or perform signal averages. In general, the computer system 700 may identify an esophageal condition that corresponds to the subject's esophageal mucosa using the same or similar methods described in FIGS. 1-6.

The input 702 may take any suitable shape or form, as desired, for operation of the computer system 700, including the ability for selecting, entering, or otherwise specifying parameters consistent with performing tasks, processing data, or operating the computer system 700. In some aspects, the input 702 may be configured to receive data, such as data acquired from a mucosal impedance catheter or a catheter system, such as those described in FIG. 2 and FIG. 8. In addition, the input 702 may also be configured to receive any other data or information considered useful for classifying or identifying the esophageal condition, for example, input patient data.

Among the processing tasks for operating the computer system 700, the one or more hardware processors 704 may also be configured to carry out any number of post-processing steps on data received by way of the input 702. For example, the processor may be configured implement the same or similar method tasks described in FIGS. 1-6. The memory 706 may contain software 710 and data 712, such as data acquired with a mucosal impedance catheter, and may be configured for storage and retrieval of processed information, instructions, and data to be processed by the one or more hardware processors 704. In some aspects, the software 710 may contain instructions directed to processing the data in order to identify the esophageal condition or generate the probability that the subject's esophageal mucosa corresponds to an esophageal condition or a set of esophageal conditions, as described in FIGS. 1-6. The software 710 may also contain instructions directed to generating corrected mucosal impedance data, for example, the memory may include correction factors for one or more impedance sensing electrode configured on the catheter in the catheter system, such as those described in FIG. 2 and FIG. 8.

Figure 8:
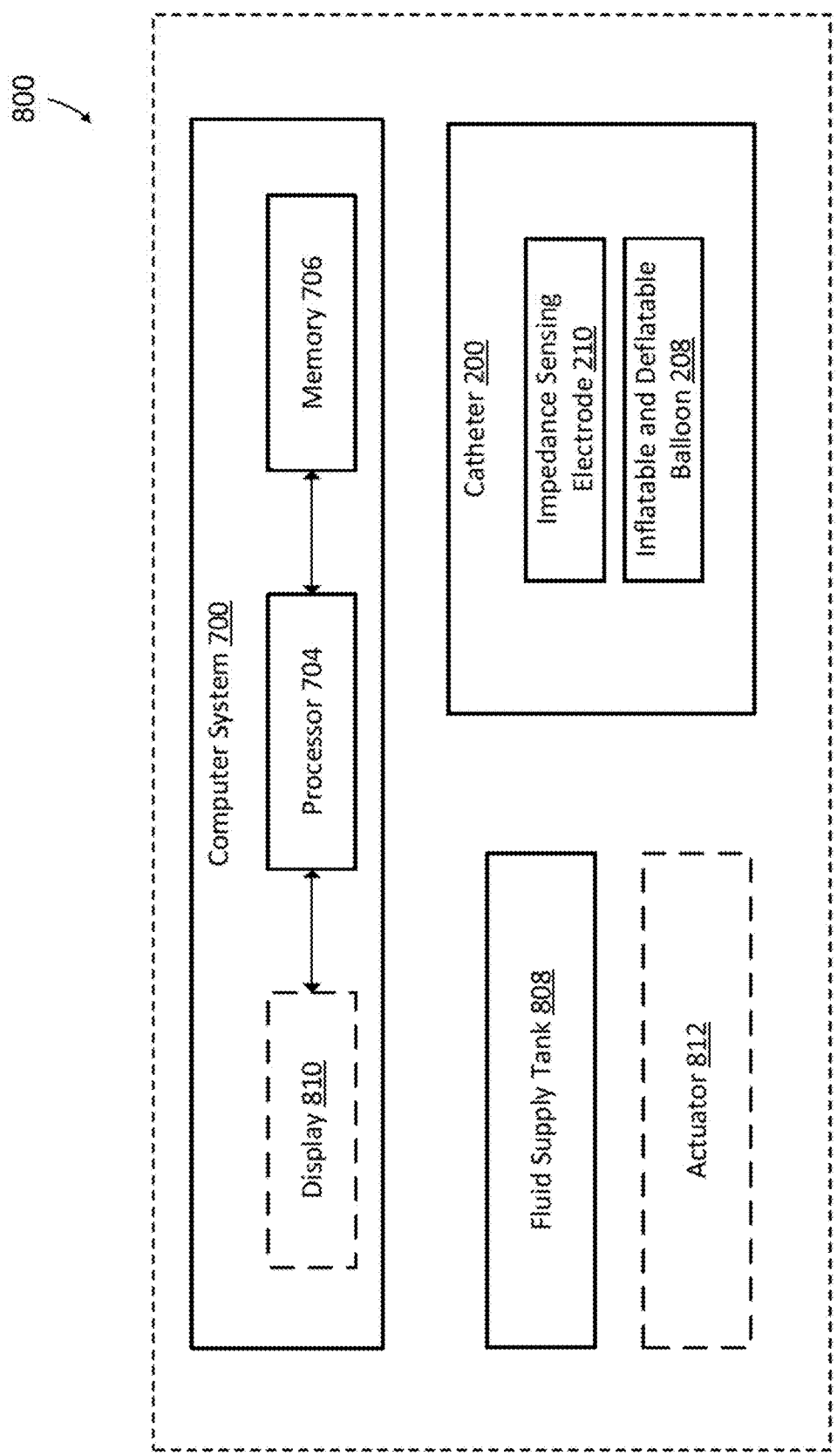
FIG. 8 is a block diagram of an example catheter system that can implement the methods in accordance with the present disclosure.

Referring particularly now to FIG. 8, an example catheter system 800 is illustrated that can implement the methods described herein, such as those described in FIGS. 1-6. In general, the catheter system 800 includes a catheter 200 configured with impedance sensing electrodes 210 and an inflatable and deflatable balloon 208, a fluid supply system 808, and the computer system 700 configured with a processor 704 and a memory 706. Optionally, the catheter system 800 may further include a display 810 and an actuator 812. The computer system 700 provides an operator interface that facilitates entering process parameters into the catheter system 800. The computer system 700 is communicatively coupled to the catheter 200, fluid supply tank 808, and actuator 812, which may be connected via a wired or wireless network connection.

The catheter 200 functions in response to instructions provided by the computer system 700 to acquire mucosal impedance data, as described in FIGS. 1-6. The fluid supply system 808 is in fluid communication with the inflatable and deflatable balloon 208. The fluid supply tank 808 functions in response to instructions provided by the computer system 700 to supply and withdraw fluid to the balloon 208 in order to place the impedance sensing electrodes 210 in contact with the subject's esophageal mucosa, as described in FIGS. 1-6. The computer system 700 may control the flow rate of fluid using values (not shown) to regulate the pressure of the inflatable and deflatable balloon 208. In some embodiments, the optional actuator 812 may be configured to displace the catheter 200 during mucosal impedance data acquisition, for example, pulling the catheter incrementally along the length of the subject's esophagus to acquire mucosal impedance data, as described in FIGS. 1-6. The catheter system 800 may further include a display used for displaying reports and graphs, such as those described in FIGS. 1-6.

Examples

The following examples set forth, in detail, ways in which the present disclosure may be used or implemented, and will enable one of ordinary skill in the art to more readily understand the principles thereof. The following examples are presented by way of illustration and are not meant to be limiting in any way.

The studies presented herein were performed in accordance with the Declaration of Helsinki, Good Clinical Practice, and applicable regulatory requirements. Each patient signed a consent form before undergoing any study-related procedures. The Vanderbilt Institutional Review Board approved this clinical trial.

Study and Patient Population

In Example 1, a population of patients were referred for diagnostic testing for GERD or EoE at the Esophageal Motility Center at Vanderbilt University Medical Center or the Mayo Clinic. Patients referred for evaluation of GERD also underwent ambulatory wireless 48 hour pH monitoring one week off acid suppressive treatment. Presenting symptoms in this group included typical symptoms of GERD (heartburn, regurgitation) or atypical symptoms (epigastric pain, chronic cough, hoarseness, and asthma) with an incomplete response to acid suppressive therapy. The following information were collected from all patients: demographic data (age, sex, race, body mass index), presence of GERD symptoms (heartburn with or without regurgitation), extra-esophageal symptoms (cough, hoarseness, epigastric/chest pain or asthma), or dysphagia. The presence and size of a hiatal hernia along with the presence and severity of esophagitis (graded by the Los Angeles Classification: A, B, C, or D) were determined with endoscopy.

In patients who were referred for evaluation of EoE, the diagnosis was confirmed by pathology (>15 eosinophils/HpF in both distal and proximal esophageal biopsies). The primary presenting symptoms in this group was dysphagia. Wireless pH testing was not conducted in patients with suspected EoE as it is not included in the current recommendations for initial evaluation of these patients. 25 Patients with age below 18 years or history of radiation, malignancy, recent esophageal surgery, known Barrett's esophagus, or narrow caliber esophagus that precluded safe expansion of the balloon MI were excluded. All patients underwent esophagogastro-duodenoscopy (EGD). Patients were stratified into those with GERD (erosive esophagitis (E+) or normal EGD with abnormal pH defined as total percent time pH<4 of >5.5%, E+/pH+), active EoE, and normal EGD/normal pH (non-GERD, E−/pH−). All patients in the study underwent the balloon MI testing during endoscopy and prior to deployment of wireless pH capsule or esophageal biopsies.

Balloon Mucosal Impedance Design

A balloon MI catheter, similar to FIG. 2, was used to measure electrical impedance of the esophageal lining by direct mucosal contact. Special sensor columns designed to detect changes in mucosal impedance were mounted on a balloon made from medical grade Polyethylene Terephthalate (PET), which is specifically used for its non-compliant properties that prevent expansion beyond 2 cms diameter. The catheter body is manufactured from medical grade PolyEther Blok Amide (PEBAX), which is routinely used in esophageal catheters and is biocompatible. The sensors were spaced at 1 cm. The initial design included four axial columns of 9 impedance channels (total of 36) separated by 90 degree intervals with length of 10 cm mounted on an inflatable balloon.

The catheter included two axial columns of 9 channels (total of 18) separated by 180 degree intervals on the balloon. Most patients (75%) underwent testing using four columns balloon MI catheter, while 25% of patients underwent testing using the two columns balloon MI catheter. The two columns on the balloon MI catheter allowed for axial pattern of MI along the esophageal axis in patients with EoE or GERD. This device is introduced into the esophagus under endoscopic guidance with the most distal sensors just above the SCJ.

Direct contact of the MI sensors with the esophageal epithelium is obtained by inflating an intra-esophageal balloon assembly in a controlled fashion using a calibrated inflation device (e.g., Boston Scientific, Marlsborough, Mass.). Inflation of the balloon allowed for direct contact of MI sensors with the esophageal epithelium by eliminating interference from the luminal fluids and gases that can significantly affect readings. The balloon assembly is attached to a channeled feed that records axial MI measurements (in ohms, $\Omega$) on a 10 cm segment of the esophagus with radial measurements from sensors at 2 or 4 columns over 90 seconds. Data is displayed in a tabular and heat map format on a dedicated computer using a software program designed by Diversatek Healthcare Inc. The frequency for the measuring circuit was set at 10 Hz. Once the MI data is recorded, the balloon assembly is deflated and then removed by the provider. The overall procedure added approximately 2-3 minutes of additional procedure time for each research participant.

Wireless pH Monitoring

All patients who were referred for diagnostic testing for GERD underwent 48 hour ambulatory wireless pH monitoring (Given Imaging, Duluth, Ga.). They were instructed to stop taking all proton pump inhibitors and H2-receptor antagonists for at least 7 days prior to undergoing ambulatory pH monitoring. The wireless device was deployed during upper endoscopy after visual anatomic inspection and distance measurements from the incisors to the SCJ. Wireless capsules were calibrated by submersion in buffer solutions at pH 7.0 and pH 1.0, and then activated by magnet removal. They were placed using the manufacturer's delivery system at 6 cm above the SCJ and attached with vacuum suction as previously described. Capsule placement was confirmed with endoscopy. Subsequently, patients were given wireless pH recorders to wear on their waists, or to keep within 3 feet to 5 feet at all times. Recording devices receive pH data sampling transmitted by the capsule at 433 Hz with 6 second sampling intervals and pH recording is conducted for a total of 48 hours. Patients were instructed to perform their normal daily activities and dietary practices. Measurements of the total, upright, supine percentage time when esophageal pH was below 4 were determined over day 1 and day 2 of the wireless study. Acid exposure time (percent time pH was <4) of greater than 5.5% per day was considered abnormal.

Statistical Analysis

MI values were processed for each subject in the following steps. First, MI values were set to missing if we observed no variability in a column over distance, a MI value was over 6000 Ohms, or a studentized residual was above 3.5. We then calculated the MI at each distance by averaging across the non-missing channels for each distance. For the 2- and 4-column catheter, we averaged over 2 and 4 values, respectively, at each distance. In addition to using the MI at each distance, we also summarized the MI using an intercept and slope. The intercept and slope were calculated by conducting separate simple linear regressions by subject using MI (outcome) and distance (continuous predictor) to estimate the intercept and slope parameter. The intercept and slope thus correspond to the proximal MI measurement and change in MI over time. Sensitivity analysis were also conducted. There was strict control and supervision of the data entry and access for this study.

Patient characteristics were described using medians and interquartile ranges (IQR, $25^{th}$ and $75^{th}$ percentiles) for continuous variables and proportions for categorical variables. Statistical differences in outcomes among groups and various esophageal sites were assessed using Kruskal-Wallis test, Pearson $X^2$ test, or the Wilcoxon test. $P<0.05$ was considered significant. Receiver operating characteristic (ROC) curves and area under the ROC curve (AUC) were used to compare predictive accuracy of balloon MI for GERD, EoE, and non-GERD subjects. Separate multivariable logistic regression models were fit either using either GERD (vs EoE and non-GERD), EoE (versus GERD and non-GERD) or non-GERD (versus GERD and EoE) as the outcome of interest. Two-predictor models with the predictors being either continuous measures of (1) MI at 2 cm and MI at 5 cm, (2) MI at 2 cm and MI at 10 cm, and (3) intercept and slope of MI (defined above). Predicted probabilities of diagnosis group (GERD, non-GERD, or EoE) as a function of MI intercept and MI slope were estimated using multinomial logistic regression. This model assumes that subjects may belong to one of the three diagnosis groups, and uses the baseline prevalence of GERD, non-GERD, and EoE (35%, 35%, 30%) to estimate conditional probability of group membership given MI intercept and slope.

Statistical differences in outcomes among groups and various esophageal sites were be assessed using Kruskal- Wallis test, Pearson $X^2$ test, or the Wilcoxon test to test the accuracy of the classification models. $P<0.05$ is generally considered significant. Receiver operating characteristic (ROC) curves and area under the ROC curve (AUC) were used to compare predictive accuracy of balloon MI for GERD, EoE, and non-GERD subjects.

Equation 1 provides one non-limiting example of a classification model that is in accordance with the present disclosure. Equation 1 shows the prediction model that the MI software can employ during endoscopy to determine probability of GERD, EoE, and non-GERD using the intercept and slope of the MI measurements from distal to proximal esophagus:

$$\text{Prob}\{diag3 == "ActiveEoE"\} = \frac{1}{1 + \exp(-X\hat{\beta})}, \text{ where}$$

$$X\hat{\beta} = 3.359829 -$$

$$0.0015040744 \text{ Intercept} - 0.0092364544 \text{ Slope}$$

$$\text{Prob}\{diag3 == "E\text{-}andpH < 5.5"\} = \frac{1}{1 + \exp(-X\hat{\beta})}, \text{ where}$$

$$X\hat{\beta} = -1.406836 +$$

$$0.0004370183 \text{ Intercept} + 0.0003099486 \text{ Slope}$$

Equation 1

The three probabilities must sum to 1, so the probability of E+ or pH>5.5=1−Pr(Active Eoe)−Pr(E− and pH<5.5).

FIG. 5 shows the heat map of predicted probabilities using equation 1 for various combinations of slope and intercept of MI measurements. As highlighted in FIG. 4, the probability of EoE is highest (blue) with low MI values distally (intercept) in the esophagus and low slope (minimal rise of MI with distance away from SCJ), while a greater rise in slope with low intercept distally is suggestive of GERD (red), and higher MI distally with higher slope is suggestive of non-GERD (gray).

Results

A total of 69 patients were studied and stratified into those with GERD (E+/pH+, n=24), active EoE (n=21), and non-GERD subjects (E−/pH−, n=24) as shown in Table 1. Overall, 83% of patients with GERD had esophagitis (LA grade A, 20%; grade B, 40%; grade C, 30%; and grade D, 10%) with 27% of them having a hiatal hernia. As expected, patients with EoE were younger with median (IQR) age of 33 years (26-38) and more likely to present with dysphagia as the primary complaint (93%) compared to non-GERD or patients with GERD (P<0.01). The median eosinophilic count/HpF was 50 (30-100) in the proximal esophagus and 47 (40-50) in the distal esophagus in patients with EoE. As expected, patients with GERD had significantly higher acid exposure time (total, upright, and supine percent time pH was <4) compared to those without GERD (E−/pH− group) (P<0.01). There were no other differences in other patient characteristics.

TABLE 1

Baseline demographics of patients.

|  | GERD (N = 24) | Non-GERD (N = 24) | Active EoE (N = 21) | P- value |
|---|---|---|---|---|
| Age | 48 (42-62) | 62 (50-67) | 33 (26-38) | <0.01[2] |
| BMI | 30 (27-35) | 27 (25-35) | 27 (25-28) | 0.09[2] |
| Female, % (n) | 54% | 71% | 33% | 0.07[1] |
| Ethnicity, % (n) |  |  |  | 0.54[1] |
| Caucasian | 92% | 92% | 100% |  |
| Black | 4% | 8% | 0% |  |
| Other | 4% | 0% | 0% |  |
| Chief Complaint, % (n) |  |  |  | <0.01[1] |
| GERD (heartburn or regurgitation) | 63% | 66% | 7% |  |
| Dysphagia | 12% | 8% | 93% |  |
| Other (atypical symptoms) | 25% | 25% | 0% |  |
| Presence of esophagitis, % (n) | 83% |  |  |  |
| A/B | 60% |  |  |  |
| C/D | 40% |  |  |  |
| Presence of hiatal hernia, % (n) | 27% | 15% | 0% | 0.14[1] |
| pH parameters |  |  |  |  |
| Total % time pH < 4 | 11.2 (9.6-14.7) | 2.7 (1.0-3.8) |  | <0.01[3] |
| Upright % time pH < 4 | 14.8 (10.6-18.4) | 3.0 (1.3-5.2) |  | <0.01[3] |
| Supine % time pH < 4 | 3.9 (2.4-6.0) | 0.1 (0-0.7) |  | <0.01[3] |
| Eosinophilic count (per HpF) |  |  |  |  |
| Proximal esophagus |  |  | 50 (30-100) |  |
| Distal esophagus |  |  | 47 (40-50) |  |

The ranges in parentheses for age, BMI, eosinophilic count, and Total/upright/supine % time pH < 4 represent the interquartile range. Test used: Pearson test;
[2]Kruskal-Wallis test; Wilcoxon test.
HpF: High power field.

Overall, median (IQR) MI measurements (11) were significantly (P<0.01) lower for the GERD and EoE groups at all esophageal sites compared to non-GERD subjects (Table 2). The axial pattern of balloon MI (measurements over distance from SCJ) was unique for those with GERD (E+/pH+), EoE, and non-GERD (E−/pH−), MI measurements were lower in the distal esophagus (closer to SCJ) and had incremental rise with distance away from the SCJ; patients with EoE had even lower baseline MI with only small rise from distal to proximal esophagus. Non-GERD subjects (E−/pH−) had higher baseline MI values in the distal esophagus and remained elevated with distance away from the SCJ. A unique esophageal mucosal contour based on balloon MI measurements (in ohms) over distance from SCJ (axial pattern) and radial pattern (measurements at 90 degree intervals). This heatmap highlights the unique characteristics of the three groups which discriminates GERD, EoE, and non-GERD and can easily be employed to establish a diagnosis during endoscopy independent of biopsy or pH monitoring.

Figure 9:
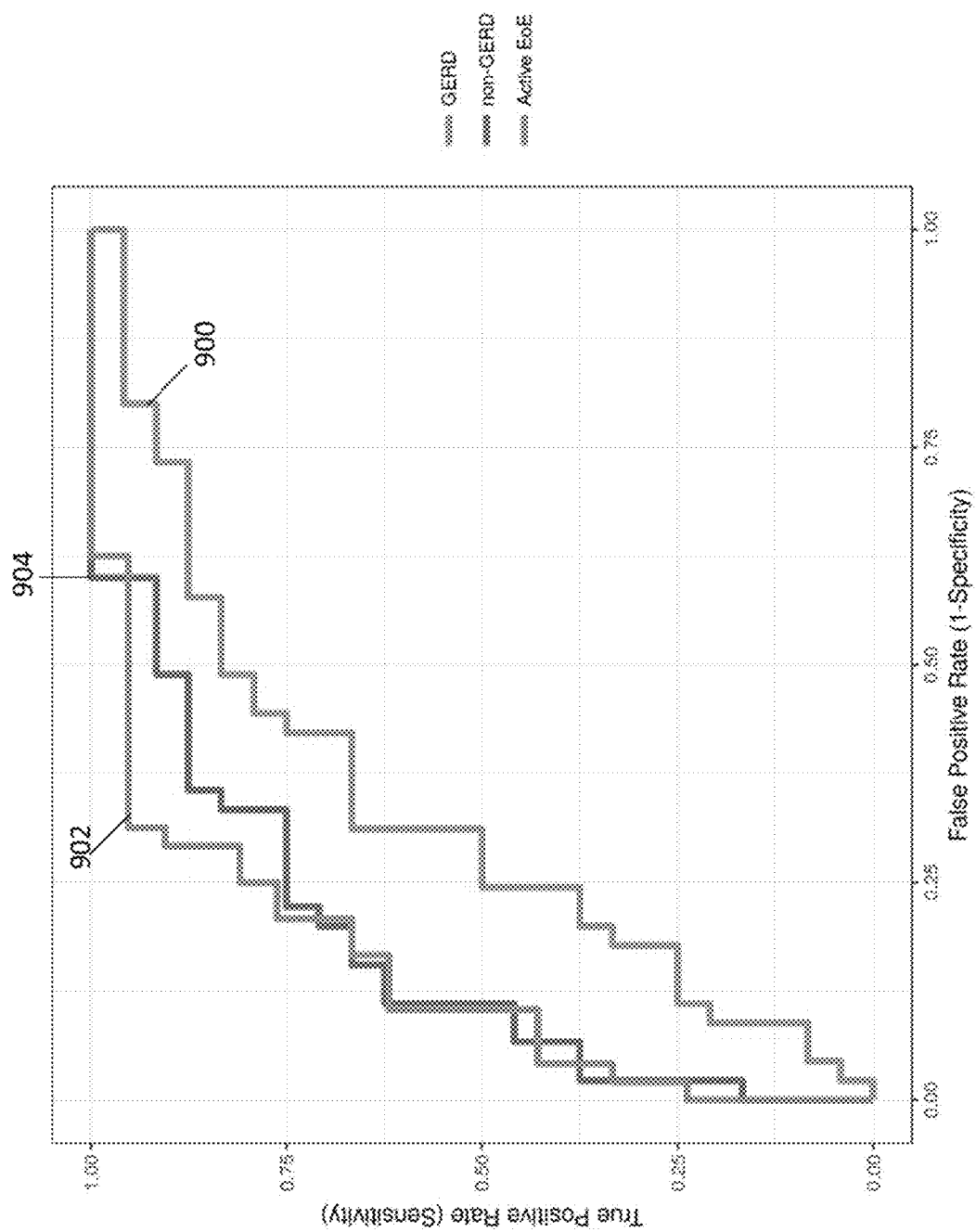
FIG. 9 is a graphical illustration of receiver operating characteristic analysis of intercept and slope of mucosal impedance measurements acquired using a catheter system in accordance with the present disclosure.

Among the tested variables, the intercept and slope (rise of MI over distance) resulted in the best fit in predicting the three groups (Table 3). Receiver operating characteristic analysis of intercept and slope of balloon MI measurements along the esophageal axis were able to reliably predict GERD (AUC=0.67), EoE (AUC=0.84), or non-GERD (AUC=0.83) as shown in FIG. 9.

other side, diagnosis for EoE has relied on obtaining distal and proximal esophageal biopsies and histopathological confirmation, which can lead to added cost burden and delay of treatment and diagnosis. There are currently no techniques that accurately, instantly, and reliably detect changes in mucosal integrity from long-term inflammation related to injurious gastroduodenal contents or from immune-mediated disease. In addition, there is also significant overlap between clinical presentation of GERD and EoE with heartburn reported in 30-60% of patients with EoE. The overlap in symptoms can make clinical separation between GERD and EoE challenging prior to diagnostic testing given both are frequently in the differential.

Furthermore, EoE can be patchy disease and while there are general recommendations on where to obtain biopsies to diagnose EoE (proximal and distal esophagus), studies have shown that only 24% of academic and 3% of community gastroenterologists follow consensus guidelines to diagnose EoE. This has also led to significant variability in diagnostic criteria used by studies for EoE in the literature ranging from 5 to 30 eosinophils/HpF with large proportion of studies (35%) not even stating their diagnostic criteria. Levels of esophageal eosinophilia has also been shown to vary widely throughout locations in the esophagus and even within biopsies themselves. Thus, there is no way to ensure that biopsies taken will not miss a diagnosis of EoE.

TABLE 2

Median mucosal impedance values (in Ohms) over distance in each group.

| Channels above squamocolumnar junction | GERD (N = 24) | Non-GERD (N = 24) | Active EoE (N = 21) | P- value |
|---|---|---|---|---|
| 1 | 1668 (971-2754) | 4198 (1911-6475) | 1046 (842-1896) | <0.01 |
| 2 | 2077 (1041-3020) | 4062 (2107-6036) | 1053 (789-1727) | <0.01 |
| 3 | 1713 (1265-4056) | 4473 (2752-6460) | 1203 (774-1816) | <0.01 |
| 4 | 2263 (1261-4763) | 5501 (3087-6643) | 1493 (938-2052) | <0.01 |
| 5 | 3103 (2346-4091) | 5215 (3737-5927) | 1706 (1013-2105) | <0.01 |
| 6 | 3226 (2331-4740) | 5000 (3940-5647) | 1813 (1003-2594) | <0.01 |
| 7 | 3595 (2637-4917) | 4592 (4181-6059) | 2106 (1018-2647) | <0.01 |
| 8 | 3595 (2637-4917) | 4592 (4181-6059) | 2106 (1018-2647) | <0.01 |
| 9 | 4190 (2444-4948) | 5089 (3986-6176) | 2371 (1268-3431) | <0.01 |
| Intercept | 1490 (653-3475) | 4095 (1990-6583) | 785 (501-1343) | <0.01 |
| Slope | 242 (115,323) | 68 (−84,186) | −12 (−80,263) | 0.04 |

The ranges in parentheses represent the interquartile range. Test used: Kruskal-Wallis test.

TABLE 3

Comparison of predictive accuracy of different models.

| | Models | C-index | Brier Score | $R^2$ | AIC |
|---|---|---|---|---|---|
| EoE | MI at 2 and 5 cm | 0.89 | 0.13 | 0.52 | 57.8 |
| | MI at 2 and 10 cm | 0.86 | 0.14 | 0.49 | 59.7 |
| | Intercept and slope | 0.89 | 0.12 | 0.55 | 54.9 |
| GERD | MI at 2 and 5 cm | 0.71 | 0.21 | 0.10 | 89.0 |
| | MI at 2 and 10 cm | 0.54 | 0.23 | 0.01 | 93.7 |
| | Intercept and slope | 0.69 | 0.21 | 0.11 | 88.5 |
| Non-GERD | MI at 2 and 5 cm | 0.81 | 0.17 | 0.33 | 75.8 |
| | MI at 2 and 10 cm | 0.84 | 0.15 | 0.41 | 70.3 |
| | Intercept and slope | 0.84 | 0.16 | 0.40 | 70.9 |

$R^2$ (correlation coefficient); AIC (Akaike information criterion).

Current diagnostic testing armamentarium for GERD primarily consists of pH monitoring (catheter or wireless) or multi-channel intraluminal impedance/pH monitoring, which are limited to detection of only intraluminal reflux events over 24- to 48-hour period and thus, only provide a "snapshot" measure of a chronic disease process. On the Overlap among clinical presentations between GERD and EoE along with inadequate reliability of endoscopic features and histopathological changes can make it challenging for a clinician to reliably choose the correct diagnostic test. Single channel mucosal impedance catheters may be subject to measurement variability due to lack of adequate contact with the mucosa and interference from intraluminal gas or fluid due to the 360° measurement by the sensors. Furthermore, the single channel catheter only allows measurement of spot impedance, which similar to biopsy specimens can be subject to diagnostic variability in patchy diseases.

In some aspects of the present disclosure, a multi-center prospective study, we showed the clinical performance using a catheter system that is easily and reliably able to distinguish patients with GERD, EoE, or non-GERD during endoscopy. The approach allows clinician to obtain MI measurements on a 10 cm segment of the esophagus, which can increase diagnostic yield especially in disease such as EoE, which can be patchy.

The present disclosure provides a catheter system that may differentiate GERD and EoE compared to non-GERD patients. The catheter system may include a classification model that, in some aspects, utilizes an intercept and slope (rate of rise of MI from distal to proximal esophagus) of MI measurements to discriminate between esophageal conditions, such as EoE, GERD, or non-GERD. The catheter system and methods presented herein may instantly provide the likely diagnosis (EoE, GERD, or non-GERD) during endoscopy, which can help reduce unnecessary testing. Our technique is safe, simple, can be performed during endoscopy, and can be performed during clinically feasible time frames.

Improvement in clinical symptoms on the other hand have low accuracy in predicting endoscopic or histologic remission in patients with EoE. Thus, MI can be a surrogate marker of histology and be used to monitor treatment response during endoscopy instead of repeated esophageal biopsies.

On the other side, reflux testing for GERD has primarily relied on detection of intraluminal acid or non-acid refluxate over 24 to 48 hour period, which has led to significant variability in sensitivity and specificity of these testing as they fail to account of chronicity of the disease. This has led to poor reliability of current reflux diagnostic testing in being able to predict response to medical or surgical therapies. Thus, focus has now shifted towards identifying novel diagnostic parameters that can assess for chronicity of reflux and detect alternations in esophagus mucosal integrity.

Current impedance devices rely on a transnasal catheter design, which is associated with significant patient discomfort and can lead to alteration in patient's daily activities, which can affect sensitivity of these tests. Transnasal probes also lose precision as they are not consistently in contact with the esophageal mucosa (due to movement in the esophageal lumen) and we have previously shown that this results in increased variability of measurements compared to direct MI measurements during endoscopy.

In some aspects of the disclosure, multi-channel mucosal impedance sensors may offer an improvement from the single channel MI catheter. For example, the use of 180° impedance sensors mounted on the exterior surface of the catheter allows precise opposition of the sensor to the mucosal lining (compared to the 360° circumferential ring design of the single channel catheter) and may reduce interference from intraluminal contents such as air and liquid. Single channel MI catheters may additionally have to be manually repositioned from one site to another along the esophagus, which can result in inter-provider variability, which may be reduced by using multi-channel impedance sensors. For example, inclusion of multiple radial and axial MI sensors on the 10 cm balloon may allow for wider sampling of esophageal mucosal integrity.

In some aspects, the classification model can be used instantly during endoscopy to predict probability of GERD, EoE, or non-GERD, which can help guide clinical decision making. The systems and methods herein improve upon previous methods that rely on arbitrary cut-offs, where cut-offs can frequently be misleading in a clinical setting. The systems and methods presented herein may provide post-test probability after MI measurements, and can aid in augmenting the clinicians pre-test probability of the disease instantly during endoscopy.

In some aspects, the classification model may assume subjects belong to a finite set of esophageal conditions, for example one of the three diagnosis groups, and uses an equal baseline prevalence of GERD, non-GERD, and EoE (35%, 35%, 30%) to estimate conditional (post-test) probability of the disease given MI intercept and slope. However, clinically, certain demographic and clinical symptoms can help us augment the pre-test probability. Such data may be provided as input data 702 to the computer system 700 or the catheter system 800. For instance, studies have shown that clinical features that independently predicted EoE were younger age (<50 years), male, symptoms of dysphagia or history of food impaction, and documented food allergies/asthma. In some aspects, the classification model may incorporate clinical characteristics to change the pre-test probability of a disease and then use balloon MI to provide more definitive post-test probability of the disease.

In some aspects, the present disclosure provides a catheter system for detecting esophageal mucosal changes due to chronic GERD or EoE instantly during endoscopy without the need for 24 to 48 hour ambulatory wireless pH monitoring or esophageal biopsies for histopathology. This helps to reduce diagnostic and treatment latency and might allow for monitoring disease activity over time.

The present disclosure has described one or more preferred embodiments, and it should be appreciated that many equivalents, alternatives, variations, and modifications, aside from those expressly stated, are possible and within the scope of the invention.

The invention claimed is:

1. A catheter system comprising:
   a catheter including an elongate shaft extending between a proximal end and a distal end;
   a plurality of impedance sensing electrodes configured between the proximal end and the distal end;
   an inflatable and deflatable balloon configured to the elongate shaft;
   a computer system communicatively coupled to the catheter, and wherein the computer system is programmed to:
      control the inflatable and deflatable balloon to expand to place at least a portion of the impedance sensing electrodes in contact with an esophageal mucosa on the interior esophageal wall of a subject;
      acquire mucosal impedance data of the esophageal mucosa at a plurality of axial positions between the distal position and the proximal position of the catheter by directing an electric current through the esophageal mucosa via the impedance sensing electrodes;
      generate a report that includes a probability that at least a portion of the subject's esophageal mucosa corresponds to one or more esophageal condition, wherein the probability is generated based at least in part on the mucosal impedance data acquired between the proximal end and the distal end of the catheter, and wherein the probability is generated using a classification model that includes a multinomial logistic regression, wherein the multinomial logistic regression generates the probability based at least in part on fitting the mucosal impedance data at two or more of the axial positions to generate a classification slope and a classification intercept, and generating the probability using the classification slope and the classification intercept.

2. The catheter system of claim 1, wherein the computer system is further programmed to:
   generate a probability that the esophageal mucosa corresponds to a set of esophageal conditions, wherein the probability is generated based at least in part on the mucosal impedance data acquired between the proximal end and the distal end of the catheter, wherein the set of esophageal conditions includes gastroesophageal reflux disease (GERD), eosinophilic esophagitis (EoE), and non-gastroesophageal reflux disease (NERD).

3. The catheter system of claim 1, wherein an exterior surface of the catheter includes at least two impedance sensing electrodes at a plurality of axial positions along the length of the catheter.

4. The catheter system of claim 1, wherein the computer system is further programmed to:
identify and remove non-contact impedance data from the acquired mucosal impedance data to generate corrected mucosal impedance data, wherein the non-contact impedance data corresponds to impedance data generated when the impedance sensing electrodes are in contact with a remnant in the subject's esophagus that is different than the esophageal mucosa, and wherein the computer system identifies and removes the non-contact impedance data if the data corresponds to one or more of the following conditions:
  (a.) acquired impedance data that exceeds a threshold impedance measurement, wherein the threshold measurement is 5000 Ohms; and
  (b.) acquired impedance data that has a studentized residual above 3.

5. The catheter system of claim 1, wherein the computer system is further programmed to:
store an individual correction factor for at least a portion of the impedance sensing electrodes in a memory of the computer system; and
generate corrected mucosal impedance data by applying the individual correction factor to the mucosal impedance data acquired by the corresponding impedance sensing electrode.

6. The catheter system of claim 5, wherein the computer system is further programmed to:
generate the individual correction factors by calibrating at least a portion of the impedance sensing electrodes using a saline solution having a known impedance and concentration.

7. A catheter system comprising:
a catheter including an elongate shaft extending between a proximal end and a distal end;
a plurality of impedance sensing electrodes configured between the proximal end and the distal end;
a computer system communicatively coupled to the catheter, and wherein the computer system is programmed to:
  acquire mucosal impedance data of esophageal mucosa on the interior esophageal wall of a subject using impedance sensing electrodes at a plurality of axial positions between the distal end and the proximal end of the catheter by directing an electric current through the esophageal mucosa via the impedance sensing electrodes;
  generate a report that includes a probability that at least a portion of the subject's esophageal mucosa corresponds to one or more esophageal condition, wherein the probability is generated based at least in part on the mucosal impedance data acquired between the proximal end and the distal end of the catheter, and
  wherein the probability is generated using a classification model that includes a multinomial logistic regression, wherein the multinomial logistic regression generates the probability based at least in part on fitting the mucosal impedance data at two or more of the axial positions to generate a classification slope and a classification intercept, and generating the probability using the classification slope and the classification intercept.

8. The catheter system of claim 7, wherein the computer system is further programmed to:
generate a probability that the esophageal mucosa corresponds to a set of esophageal conditions, wherein the probability is generated based at least in part on the mucosal impedance data acquired between the proximal end and the distal end of the catheter, wherein the set of esophageal conditions includes gastroesophageal reflux disease (GERD), eosinophilic esophagitis (EoE), and non-gastroesophageal reflux disease (NERD).

9. The catheter system of claim 7, wherein an exterior surface of the catheter includes at least two impedance sensing electrodes at a plurality of axial positions along the length of the catheter.

10. The catheter system of claim 7, wherein the computer system is further programmed to:
identify and remove non-contact impedance data from the acquired mucosal impedance data to generate corrected mucosal impedance data, wherein the non-contact impedance data corresponds to impedance data generated when the impedance sensing electrodes are in contact with a remnant in the subject's esophagus that is different than the esophageal mucosa, and wherein the computer system identifies and removes the non-contact impedance data if the data corresponds to one or more of the following conditions:
  (a.) acquired impedance data that exceeds a threshold impedance measurement, wherein the threshold measurement is 5000 Ohms; and
  (b.) acquired impedance data that has a studentized residual above 3.

11. The catheter system of claim 7, wherein the computer system is further programmed to:
store an individual correction factor for at least a portion of the impedance sensing electrodes in a memory of the computer system; and
generate corrected mucosal impedance data by applying the individual correction factor to the mucosal impedance data acquired by the corresponding impedance sensing electrode.

12. The catheter system of claim 11, wherein the computer system is further programmed to:
generate the individual correction factors by calibrating at least a portion of the impedance sensing electrodes using a saline solution having a known impedance and concentration.

* * * * *

UNITED STATES PATENT AND TRADEMARK OFFICE
CERTIFICATE OF CORRECTION

PATENT NO. : 11,291,382 B2
APPLICATION NO. : 16/429992
DATED : April 5, 2022
INVENTOR(S) : Michael F. Vaezi et al.

It is certified that error appears in the above-identified patent and that said Letters Patent is hereby corrected as shown below:

In the Specification

Column 19, Line 1, "(11)" should be --($\Omega$)--.

Signed and Sealed this
Fourteenth Day of June, 2022

*Katherine Kelly Vidal*
Katherine Kelly Vidal
*Director of the United States Patent and Trademark Office*